(12) United States Patent
Boger et al.

(10) Patent No.: US 9,918,959 B2
(45) Date of Patent: Mar. 20, 2018

(54) TLR-INDEPENDENT SMALL MOLECULE ADJUVANTS

(71) Applicants: The Scripps Research Institute, LaJolla, CA (US); Board of Regents of the University of Texas System, Austin, Austin, TX (US)

(72) Inventors: Dale Boger, LaJolla, CA (US); Bruce Beutler, Irving, CA (US)

(73) Assignees: The Board of Regents of the University of Texas System, Austin, TX (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/502,117

(22) PCT Filed: Aug. 5, 2015

(86) PCT No.: PCT/US2015/043830
§ 371 (c)(1),
(2) Date: Feb. 6, 2017

(87) PCT Pub. No.: WO2016/022700
PCT Pub. Date: Feb. 11, 2016

(65) Prior Publication Data
US 2017/0224653 A1    Aug. 10, 2017

Related U.S. Application Data

(60) Provisional application No. 62/033,918, filed on Aug. 6, 2014.

(51) Int. Cl.

| | |
|---|---|
| C07D 307/79 | (2006.01) |
| C07D 333/50 | (2006.01) |
| A61K 31/343 | (2006.01) |
| A61K 31/167 | (2006.01) |
| A61K 31/381 | (2006.01) |
| A61K 31/404 | (2006.01) |
| A61K 31/4439 | (2006.01) |
| C07D 307/85 | (2006.01) |
| A61K 39/39 | (2006.01) |
| C07D 209/42 | (2006.01) |
| C07D 405/12 | (2006.01) |
| C07D 401/12 | (2006.01) |
| C07D 409/12 | (2006.01) |
| A61K 31/498 | (2006.01) |
| C07D 403/12 | (2006.01) |
| A61K 31/506 | (2006.01) |
| C07C 237/44 | (2006.01) |

(52) U.S. Cl.
CPC .......... *A61K 31/343* (2013.01); *A61K 31/167* (2013.01); *A61K 31/381* (2013.01); *A61K 31/404* (2013.01); *A61K 31/4439* (2013.01); *A61K 31/498* (2013.01); *A61K 31/506* (2013.01); *A61K 39/39* (2013.01); *C07C 237/44* (2013.01); *C07D 209/42* (2013.01); *C07D 307/85* (2013.01); *C07D 401/12* (2013.01); *C07D 403/12* (2013.01); *C07D 405/12* (2013.01); *C07D 409/12* (2013.01); *C07C 2601/14* (2017.05)

(58) Field of Classification Search
CPC .. A61K 31/343; A61K 31/167; A61K 31/381; A61K 31/404; A61K 31/4439; C07D 237/26; C07D 333/50
See application file for complete search history.

(56) References Cited

U.S. PATENT DOCUMENTS

| | | |
|---|---|---|
| 8,618,324 B2 | 12/2013 | Ahn |
| 8,895,577 B2 | 11/2014 | Wu et al. |
| 9,050,376 B2 | 6/2015 | Carson et al. |
| 2013/0165455 A1 | 6/2013 | Carson et al. |

OTHER PUBLICATIONS

Shaginian et al., J. Am. Chem. Soc., 2009, 131:5564-5572.
International Search Report PCT/US2015/043830 dated Jun. 13, 2016.

*Primary Examiner* — Sahar Javanmard
(74) *Attorney, Agent, or Firm* — Husch Blackwell LLP

(57) ABSTRACT

A TLR-independent adjuvant compound that corresponds in structure to Formula I, below, or its pharmaceutically acceptable salt is disclosed in

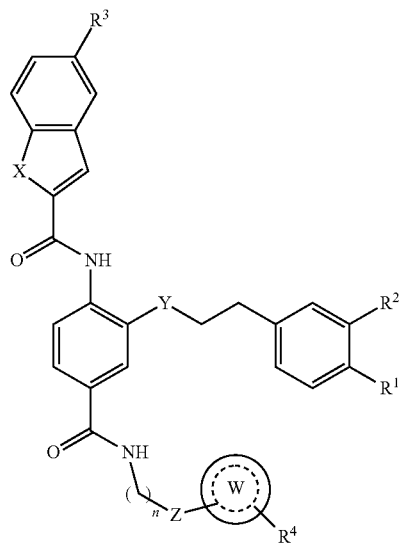

which X, Y, Z, n, $R^1$, $R^2$, $R^3$, $R^4$ and W are defined within. Also disclosed are a method of its preparation and use, as well as a pharmaceutical composition containing the same.

15 Claims, 4 Drawing Sheets

TLR-INDEPENDENT SMALL MOLECULE ADJUVANTS

CROSS-REFERENCE TO RELATED APPLICATION

This application claims priority of provisional application Ser. No. 62/033,918, filed on Aug. 6, 2014, whose disclosures are incorporated by reference.

GOVERNMENTAL SUPPORT

The present invention was made with governmental support pursuant to grant AI082657 from the National Institutes of Health/National Institute of Allergy and Infectious Diseases. The government has certain rights in the invention.

TECHNICAL FIELD

The present invention contemplates a small molecule adjuvant compound, and particularly a group of well-defined compounds that induce the secretion of TNF-α in macrophage preparations and provide immunostimulation without the apparent intervention of one or more of the TLR family of molecules.

BACKGROUND ART

The innate immune system is the first line of defense against infection and is thought to primarily be mediated by phagocytic immune cells such as macrophages and dendritic cells. These cells recognize microorganisms via a limited number of germline-encoded pattern recognition receptors (PRRs) that recognize microbial components known as pathogen-associated molecular patterns, which are essential for the survival of the microorganism and, therefore, difficult for the microorganism to alter.

Several classes of PRRs, including cell surface-located Toll-like receptors (TLRs) and cytoplasmic receptors, recognize distinct microbial components and directly activate immune cells, triggering intracellular signaling cascades that rapidly induce the expression of a variety of inflammatory cytokines that initiate a variety of overlapping immune responses. At least thirteen different TLRs have been identified in animals ranging from fruit flies to humans and mice [Beutler, *Blood*, 113:1399-1407 (2009)]. One of the best known PRRs is TLR4, which recognizes the major Gram-negative bacterial surface component lipopolysaccharide (LPS) [Akira et al., *Cell* 124:783-801 (2006)]. See also, Beutler, *Blood*, 113:1399-1407 (2009), and Moresco et al., *Curr. Biol.* 21(13):R488-93, (2011) and the citations therein for a historical perspective of the research done in finding TLRs and determining the function of TLRs.

Most of the TLRs are functional multimers. Some are heteromeric. Some appear to be homomeric, and in some cases, non-TLR subunits are part of the signaling complex. For example, TLR4 seems not to detect LPS directly, but only as a complex with MD-2, a small secreted protein that is tightly associated with the TLR4 ectodomain. Crystallographic analysis has shown the nature of the interaction between specific TLR ligands and the Toll-like receptors, including interactions between LPS and the MD-2:TLR4 complex. Beutler, *Blood* 113:1399-1407 (2009).

Studies on TLR4 signaling in monocytes, macrophages, and dendritic cells have revealed that engagement of the MD-2:TLR4 complex (hereinafter just "TLR4", for ease in expression) by LPS triggers a signaling cascade involving several intracytoplasmic and nuclear transcriptional factors. TLR4 activation first engages a set of adaptor family members that link TLR4 to the serine/threonine kinases. These kinases mediate phosphorylation and ubiquitination of various substrates, eventually resulting in the activation of the transcriptional factor NF-κB, which regulates the expression of several immunomodulatory cytokines [Kawai et al., *Cell Death Differ* 13:816-825 (2006)].

Freund's adjuvant (mycobacteria in mineral or vegetable oils), aluminum hydroxide ("alum"), and LPS (lipopolysaccharide) have been used to augment antibody responses to co-administered proteins. In the US, only alum is approved for use in human vaccines.

Of these adjuvants, only LPS and its derived lipid A have a well-defined target-TLR4, but the toxicity of these TLR4 ligands is considerable as is their instability in vivo and they are not easily conjugated to antigens.

In work that provides a powerful paradigm for synthetic "unnatural" adjuvant discovery, we identified a new class of robust small molecule adjuvants that: (1) emerged from screening an α-helix mimetic library, (2) act by an undefined mechanism that is independent of TLR4, (3) are easy to produce and structurally manipulate, (4) are non-toxic, and (5) elicit improved and qualitatively different responses from LPS. Such adjuvants may be used for co-administration or for covalently-tethered vaccination against any microbe susceptible to antibody-based protective immunization.

BRIEF SUMMARY OF THE INVENTION

The present invention contemplates a TLR4-independent immunoadjuvant compound that does not exhibit the toxicity of LPS while exhibiting activation of many similar cellular signaling pathways. A contemplated compound corresponds in structure to Formula I, below, or its pharmaceutically acceptable salt,

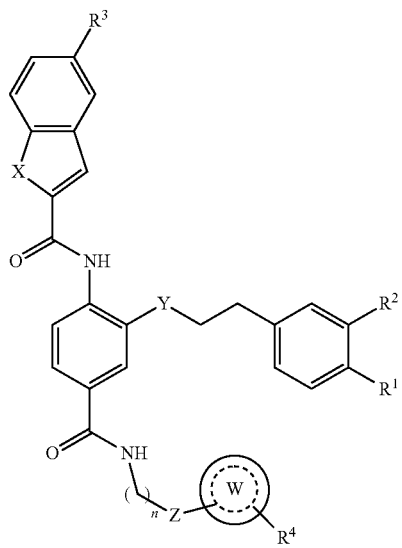

wherein:
X is O, S, $NR^5$, or $CH_2$, where $R^5$ is hydrido (H), or $C_1$-$C_4$ hydrocarbyl;
Y is O, $CH_2$, or absent;

Z is O, S, NR⁶, or CH₂, where R⁶ is hydrido (H), or $C_1$-$C_4$ hydrocarbyl;

n is a number that is zero, 1 or 2, but n is only zero when Z is CH₂;

R¹ is H or OH, R² is H or OH, or R¹ is OH and R² is OH, but at least one of R¹ and R² is OH;

R³ is hydrido (H), halogen (F, Cl or Br), azido (N₃), $C_1$-$C_4$ hydrocarbyl, $C_1$-$C_4$ hydrocarbyloxy or trifluoromethyl (CF₃);

R⁴ is hydrido, halogen, azido, $C_1$-$C_4$ hydrocarbyl, $C_1$-$C_4$ hydrocarbyloxy or trifluoromethyl;

W is a ring structure, preferably an aromatic ring structure, that contains one or two rings and includes 5 to 12 atoms in the ring structure. That ring structure W optionally contains a) 1, 2, 3 or 4 heteroatoms that are independently oxygen, nitrogen or sulfur, and contains b) one to three substituent groups (collectively referred to as R⁴) that include one or more substituents selected from the group consisting of hydrido (H), hydroxyl (OH), $C_1$-$C_4$ hydrocarbyl, $C_1$-$C_4$ hydrocarbyloxy, halogen, and trifluoromethyl bonded to one or more ring atoms. A dotted line (- - - -) represents one or more optionally present ethylenic (—C═C—) bonds.

In separate preferences as to a compound of Formula I, a) X is O or NR⁵; and b) Y is O.

One preferred compound of Formula I is a compound of Formula II, below. In Formula II, W, Z,

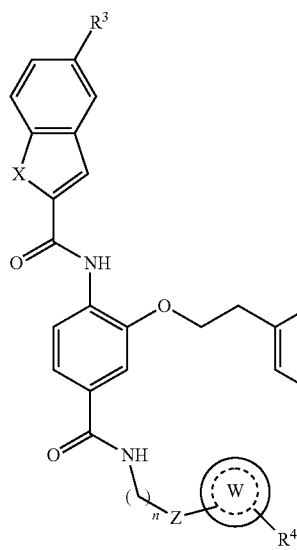

II n, R¹, R², R³, R⁴ and R⁵ are as defined for Formula I, and X is O or NR⁵. Preferably in a compound of Formula II, ring structure W is a single six-membered aromatic ring structure (aryl or heteroaryl group), X is O, and Z is CH₂.

A preferred compound of Formula II thus corresponds in structure to Formula III, below, where

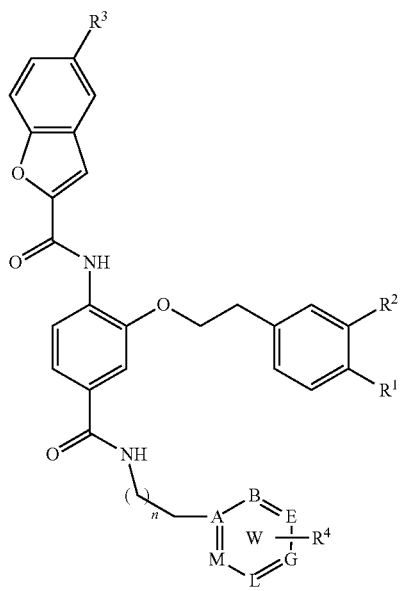

III n, R¹, R², R³, and R⁴ are as defined in Formula I. Here, W is a six-membered aromatic ring structure whose ring atoms: A, B, E, G, L and M are carbon (C) or nitrogen (N) atoms, with no more than two of A, B, E, G, L and M being nitrogen.

Preferably, six-membered aromatic ring structure W is a phenyl ring and R⁴ is a single substituent that is a meta- or para-substituted halogen, azido, $C_1$-$C_4$ hydrocarbyl, $C_1$-$C_4$ hydrocarbyloxy, or a trifluoromethyl group. In another preference, R² is hydrido and R¹ is hydroxyl.

A preferred compound of Formula III thus corresponds in structure to Formula IV, below, where n, R³, and R⁴ are as previously defined.

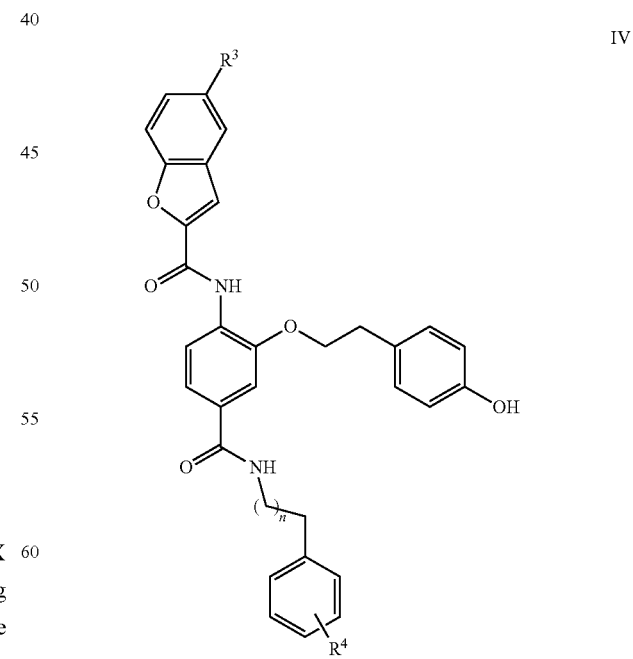

IV

Particularly preferred compounds of Formula II and Formula IV are shown below. Data that illustrate the in vitro efficacy of these compounds are shown hereinafter along with data for additional contemplated compounds.
Compound 125-03
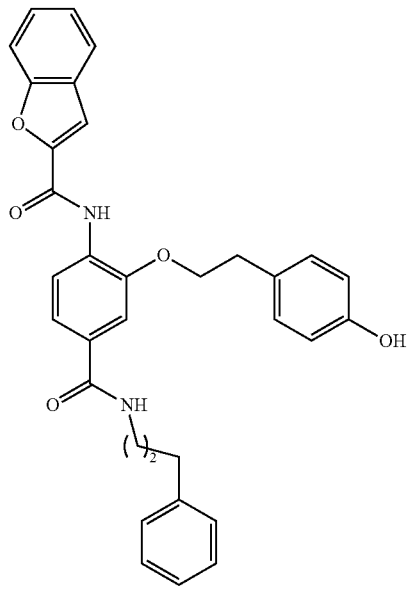
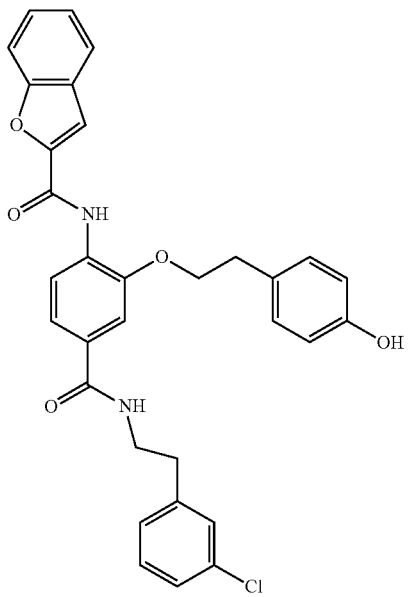
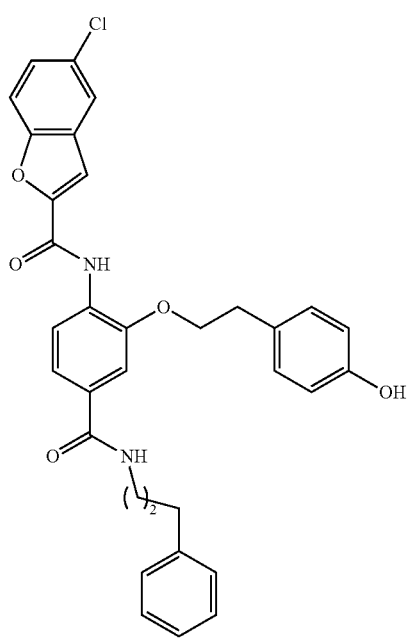
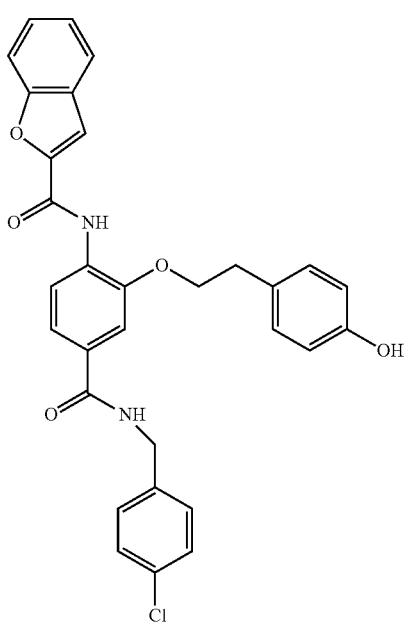

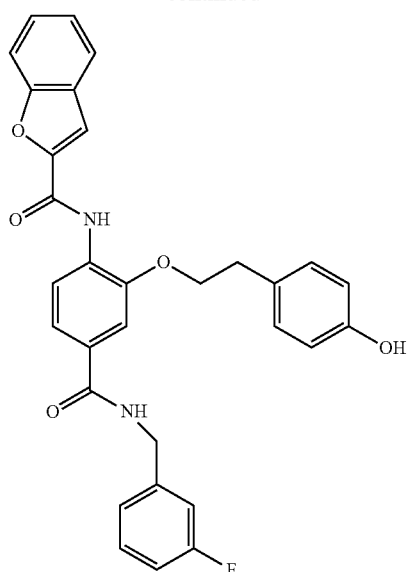
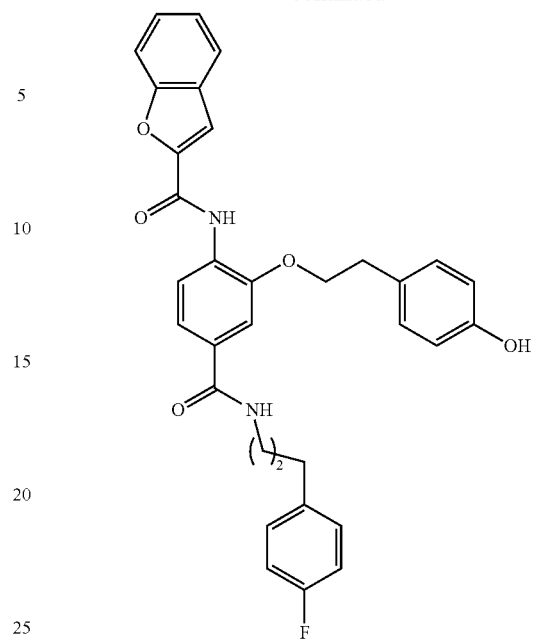
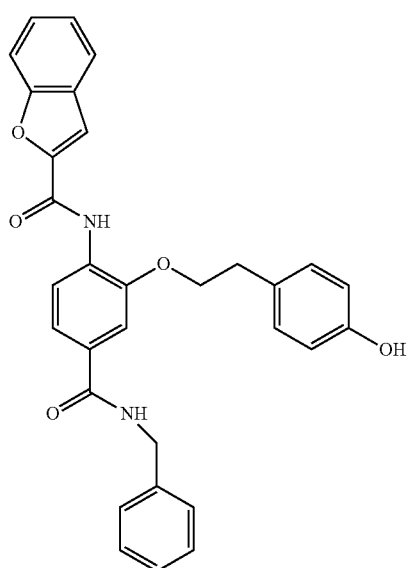
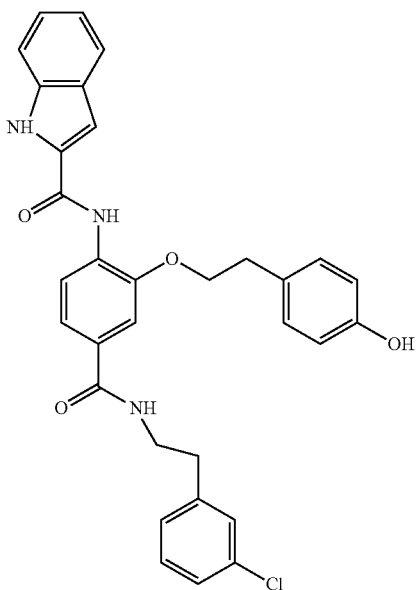

9
-continued
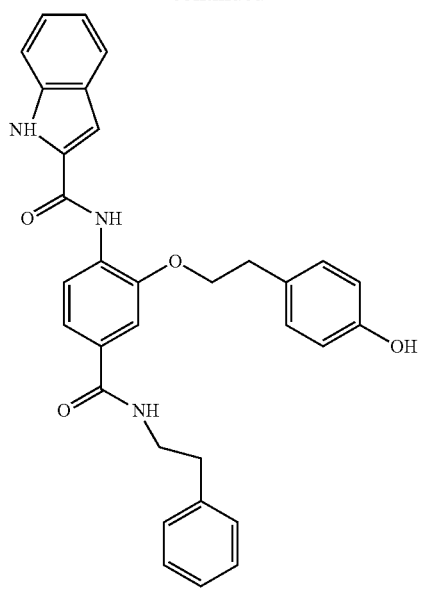
10
-continued
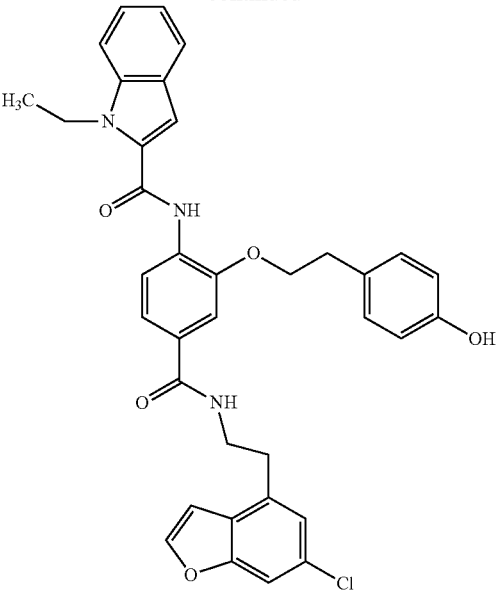
Illustrative further compounds of Formula I are illustrated below.
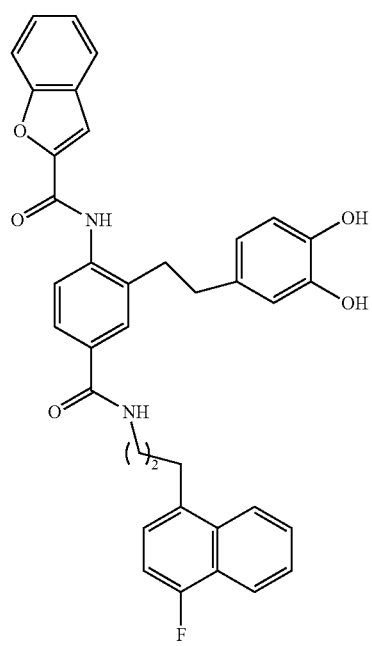
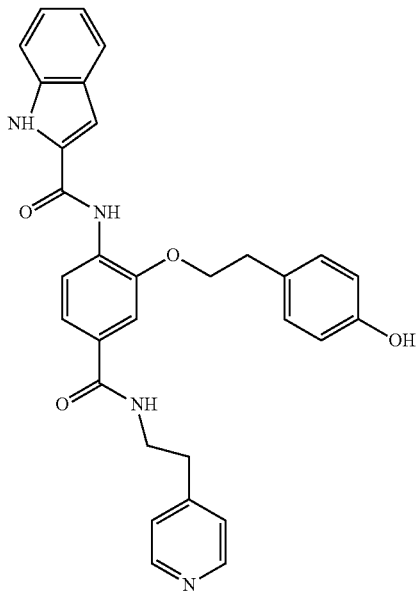

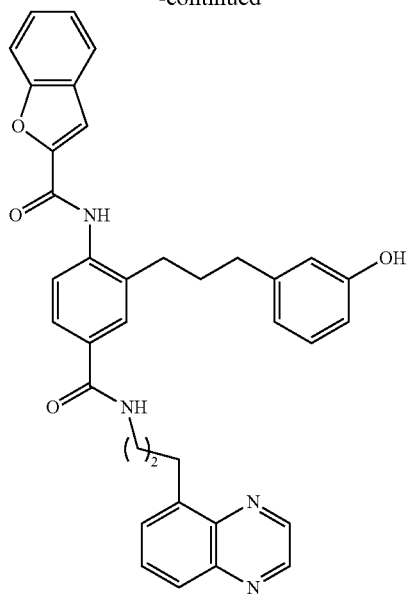
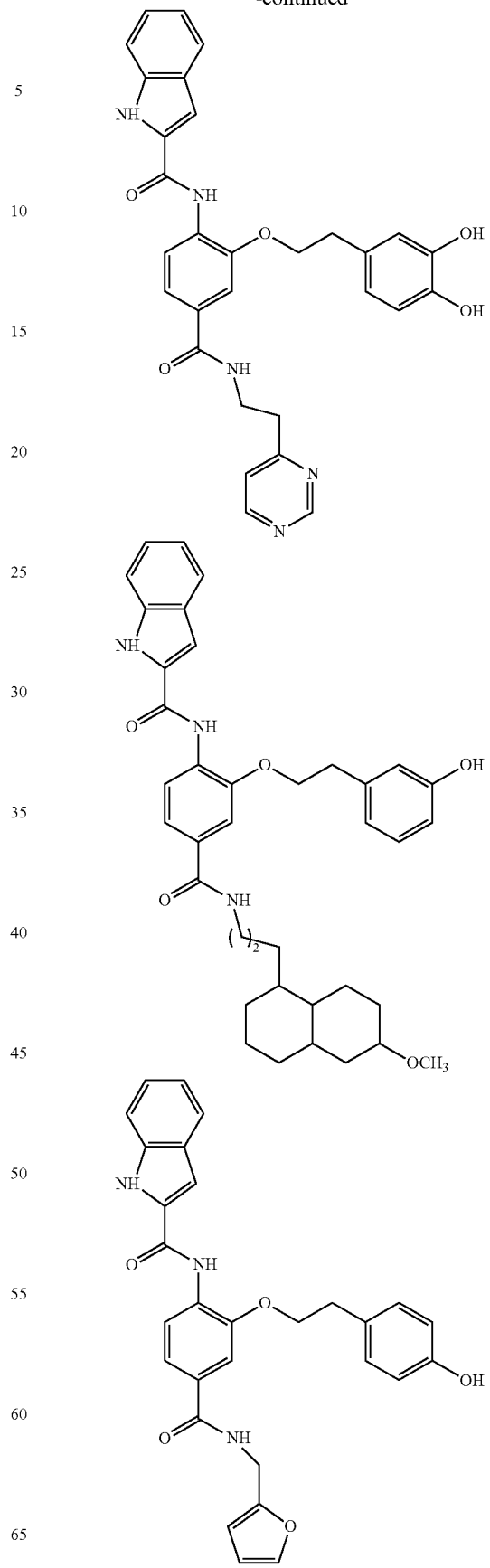

-continued

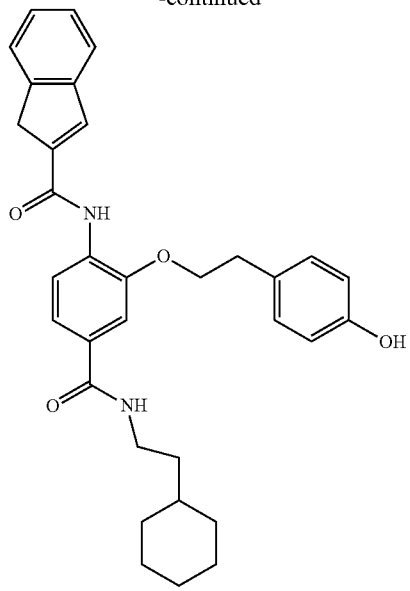

A pharmaceutical composition that contains an adjuvant effective amount of a compound of Formula I or a pharmaceutically acceptable salt thereof dissolved or dispersed in a physiologically acceptable carrier is also contemplated.

An improved method of vaccination is also contemplated. Here, mammalian cells in need of vaccination are contacted with an immunizing composition that comprises an immunoeffective amount of an immunogen and an adjuvant effective amount of an adjuvant. The improvement in this method comprises use of a compound or a pharmaceutically acceptable compound salt of Formula I as the adjuvant.

BRIEF DESCRIPTION OF THE DRAWINGS

In the drawings forming a portion of this disclosure,

In FIG. 3, adjuvants were mixed with ovalbumin (OVA, 100 μg) and injected intramuscularly into C57BL/6J mice at the indicated doses. Two immunizations were administered with a booster given at 7 days. Serum levels of OVA-specific IgG were measured (ELISA) on day 35 post-immunization, and illustrate that Compound 125-03 exhibits robust, dose-dependent adjuvant activity.

FIG. 4 provides a series of graphs that show anti-olvalbumin titers at 14 days post immunization using adjuvants with ovalbumin (OVA, 100 μg) and injected intramuscularly into C57BL/6J mice. The adjuvants used were Compound 125-03, neoseptin-3 (below), LPS, MPLA (monophosphoryl lipid A from

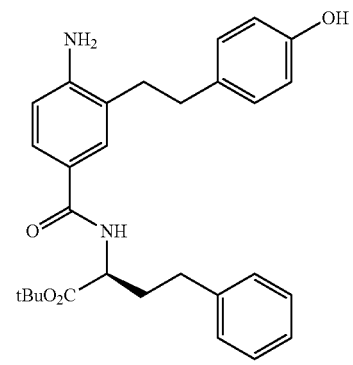

Neoseptin-3

Figure 1:
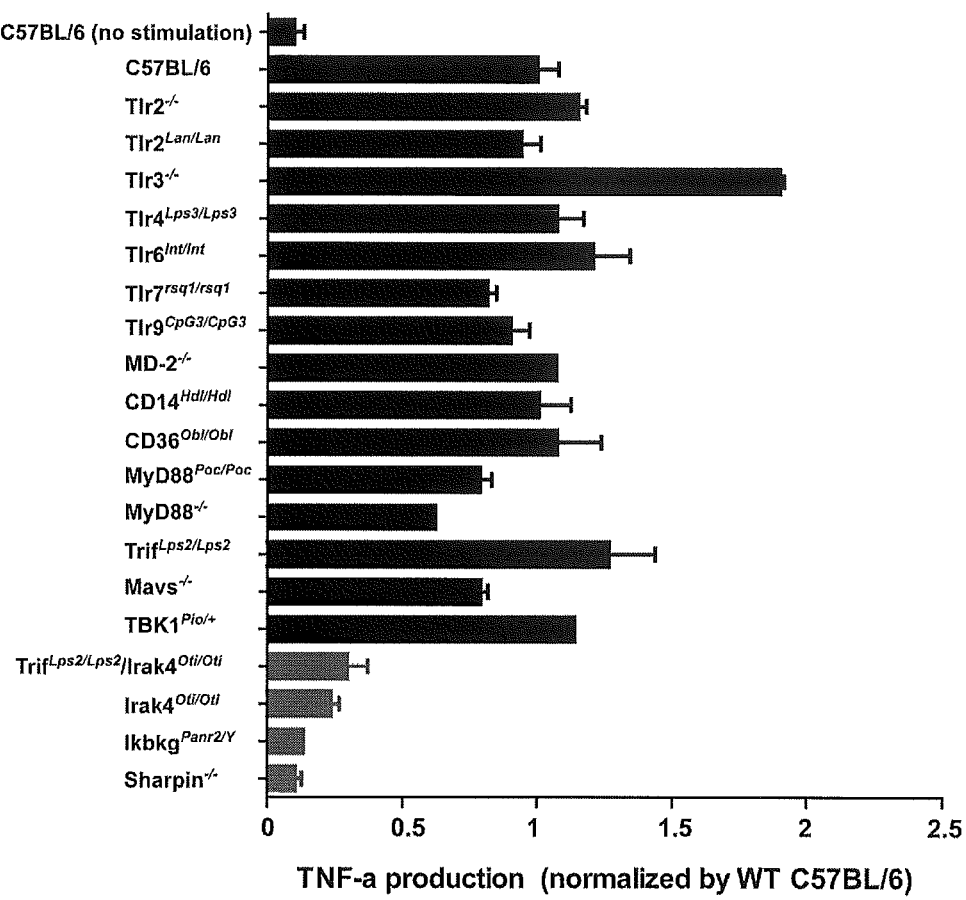
FIG. 1 shows a series of bar graphs that illustrate an assay of normalized TNF-α production in macrophages from mice containing disabling germline mutations or knockouts of genes encoding TLRs and downstream signaling proteins showing the stimulated TNF-alpha production by Compound 125-03 is independent of the TLRs including TLR4/MD-2.

*Salmonella minnesota* R595), and alum in the amounts shown. n=3.

The present invention has several benefits and advantages. One benefit is that discovery of molecularly well-defined and easily structurally manipulated adjuvants to replace the ill-defined Freund's adjuvant or alum (aluminum hydroxide) and toxic LPS is a major advance.

An advantage is that an adjuvant developed can be useful in the prevention of premature death by infections. The small molecules disclosed are more promising adjuvant candidates than the natural ligands (LPS or lipid A), being easier to produce and structurally manipulate, and they are less toxic, eliciting improved and qualitatively different responses than LPS or lipid A, while acting via mediating receptors different from LPS or lipid A that utilize one or more TLR receptors such as TLR4.

Still further benefits and advantages will be apparent to the skilled worker from the disclosures that follow.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The word "antigen" has been used historically to designate an entity that is bound by an antibody and also to designate the entity that induces the production of the antibody. More current usage limits the meaning of antigen to that entity bound by an antibody, whereas the word "immunogen" is used for the entity that induces antibody production. That more current usage will be followed herein.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or tert-butyl. Exemplary hydrocarbyl groups contain a chain of 1 to 4 carbon atoms, and preferably 1 or 2 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl. Examples of suitable alkenyl radicals include ethenyl (vinyl), 2-propenyl, 3-propenyl, 1,4-butadienyl, 1-butenyl, 2-butenyl, and 3-butenyl. Examples of alkynyl radicals include ethynyl, 2-propynyl, 1-propynyl, 1-butynyl, 2-butynyl, 3-butynyl, and 1-methyl-2-propynyl.

As a skilled worker will understand, a substituent that cannot exist such as a $C_1$ alkenyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, and tert-butoxy groups.

The term "ring structure" is used herein to mean a cyclic substituent that can contain a single ring such as an imidazolyl or phenyl group, or two fused rings as are present in a naphthyl, purinyl, or decalinyl group, or two linked rings as are present in a biphenyl group.

The term "cyclohydrocarbyl" or "carbocyclic", alone or in combination, means a cyclic hydrocarbyl radical (or ring) that contains 5 to about 12 carbon atoms, preferably about 5 to about 10 carbon atoms. Examples of such cyclohydrocarbyl radicals include cyclopropyl, cyclobutyl, cyclopentenyl, cyclohexyl, cycloheptynyl, 1- and 2-decalinyl and the like.

The term "aryl", alone or in combination, means an aromatic ring system. Such a ring system includes a phenyl, naphthyl and biphenyl ring system.

The heterocyclyl (heterocyclo) is a single 5- or 6-membered ring or a fused or linked 5,5- 5,6- 6,6-ring system that contains 1 to 4 hetero atoms (non-carbons) in the ring that independently are nitrogen, oxygen or sulfur atoms in a saturated or partially unsaturated ring. Examples of such heterocyclyl groups are pyrrolidinyl, piperidinyl, piperazinyl, morpholinyl, thiamorpholinyl, oxathiazolyl, 1,2,3-triazolyl, 1,2,4-triazolyl, pyrazolyl, 1,2,4-oxadiazinyl and azepinyl groups and a bipiperidinyl group.

A "heteroaryl" group is an aromatic heterocyclic ring that preferably contains one, or two, or three or four atoms in the ring other than carbon. Those heteroatoms can independently be nitrogen, sulfur or oxygen. A heteroaryl group can contain a single 5- or 6-membered ring or a fused ring system having two 6-membered rings or a 5- and a 6-membered ring, or a linked 5,5-, 5,6- or 6,6-membered rings as in a bipyridinyl group. Exemplary additional heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isox- azolyl, thiazolyl, 1,2,3-, 1,2,4-, 1,2,5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

Each of the four ring systems discussed above is encompassed by the ring system W. The phrase "aromatic ring system" is intended to include both aryl and heteroaryl ring groups. Each of those ring systems can optionally carry one or more substituent groups that contain a total of up to 8 atoms selected from the group consisting of fluorine, chlorine, carbon, nitrogen, oxygen and sulfur, and mixtures thereof. Hydrogens are not counted in the total number of atoms present in the one or more substituents.

DETAILED DESCRIPTION OF THE INVENTION

The present invention contemplates a Compound of Formula I or a pharmaceutically acceptable salt thereof, a pharmaceutical composition containing an adjuvant-effective amount of such a compound or its salt, and a method of using a compound or its pharmaceutically acceptable salt. More particularly, a contemplated compound corresponds in structure to Formula I, below.

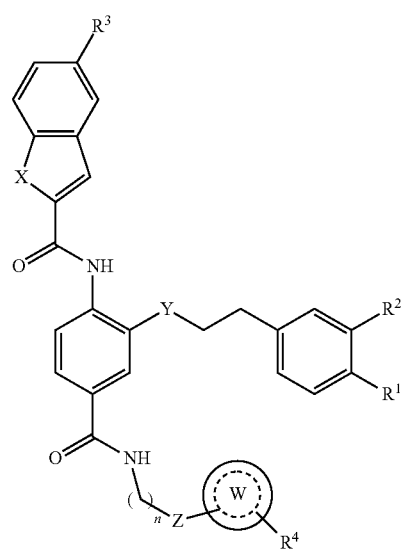

I wherein:
X is O, S, $NR^5$, or $CH_2$, where $R^5$ is hydrido (H), or $C_1$-$C_4$ hydrocarbyl;
Y is O, $CH_2$, or absent;
Z is O, S, $NR^6$, or $CH_2$, where $R^6$ is hydrido (H), or $C_1$-$C_4$ hydrocarbyl;
n is a number that is zero, 1 or 2, but n is only zero when Z is $CH_2$;
$R^1$ is H, or OH, $R^2$ is H, or OH, or $R^1$ is OH and $R^2$ is OH, but at least one of $R^1$ and $R^2$ is OH;
$R^3$ is hydrido (H), halogen (F, Cl or Br), azido ($N_3$), $C_1$-$C_4$ hydrocarbyl, $C_1$-$C_4$ hydrocarbyloxy or trifluoromethyl ($CF_3$);
$R^4$ is hydrido, halogen, azido, $C_1$-$C_4$ hydrocarbyl, $C_1$-$C_4$ hydrocarbyloxy or trifluoromethyl;

W is a ring structure, preferably an aromatic ring structure, that contains one or two rings and includes 5 to 12 atoms in the ring structure, preferably 5 to 10 atoms, and more preferably 5 or 6 atoms in the ring. That ring structure W optionally contains a) 1, 2, 3 or 4 heteroatoms that are independently oxygen, nitrogen or sulfur, and contains b) one to three substituent groups (collectively referred to as $R^4$) that include one or more substituents selected from the group consisting of hydrido (H), hydroxyl (OH), $C_1$-$C_4$ hydrocarbyl, $C_1$-$C_4$ hydrocarbyloxy, halogen, and trifluoromethyl bonded to one or more ring atoms. Preferred substituents include azido, fluoro, chloro, methyl, methoxy and trifluoromethyl groups. A dotted line (- - - -) represents one or more optionally present ethylenic (—C=C—) bonds. Where $R^4$ is two or three substituents, those substituents are referred to individually as $R^{4a}$, $R^{4b}$, and $R^{4c}$, respectively, as are present.

A ring system W is preferably aromatic or heteroaromatic (aryl or heteroaryl), as compared to being cyclohydrocarbyl or heterocyclo, so that the optional double bonds are present. It is also preferred that up to four hetero atoms are present and that those heteroatoms are each nitrogen. It is more preferred that there are one or two nitrogen atoms in ring system W.

Looking broadly, illustrative W ring systems include cyclopentenyl, cyclohexyl, cycloheptynyl, cyclooctyl, 1- and 2-decalinyl, phenyl, naphthyl, biphenyl, pyrrolidinyl, piperidinyl, piperazinyl, morpholinyl, thiamorpholinyl, oxathiazolyl, 1,2,3-triazolyl, 1,2,4-triazolyl, pyrazolyl, 1,2,4-oxadiazinyl, azepinyl, bipyridinyl, pyridyl, pyrazyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, isothiazolyl, benzothiofuranyl, isobenzothiofuranyl, benzisoxazolyl, benzoxazolyl, purinyl, anthraniloyl, 1,2-, 1,4-, 2,3- and 2,1-benzopyronyl, quinolinyl, isoquinolinyl, cinnolinyl, quinazolinyl, and 1,4-benzoxazinyl groups.

A single aromatic 6- or 5-membered ring is a preferred W ring system. Such a preferred ring system is illustrated by a phenyl, pyridyl, pyrazyl, pyrimidinyl, pyridazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and an isothiazolyl group. Phenyl, pyridyl, pyrazyl, pyrimidinyl, imidazyl and furanyl groups are more preferred, with phenyl being presently particularly preferred.

In separate preferences as to a compound of Formula I, a) X is O or $NR^5$; and b) Y is O, and most preferably, both X and Y are O.

One preferred compound of Formula I is a compound of Formula II, below. In Formula II, W, Z,

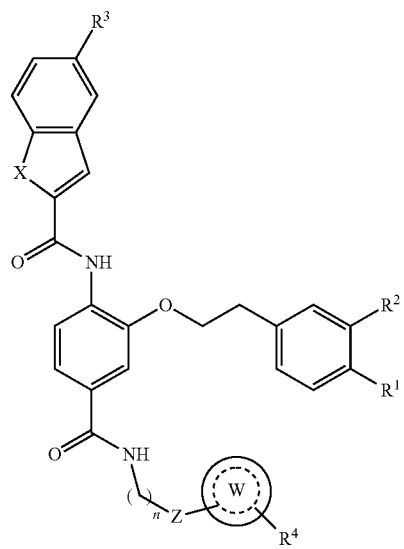

n, $R^1$, $R^2$, $R^3$, $R^4$ and $R^5$ are as defined for Formula I, and X is O or $NR^5$. Preferably in a compound of Formula II, ring structure W is a single six-membered aromatic ring structure (aryl or heteroaryl group) such as a phenyl, pyridyl, pyrimidinyl or pyrazinyl group, X is O, and Z is $CH_2$.

A preferred compound of Formula II thus corresponds in structure to Formula III, below, where

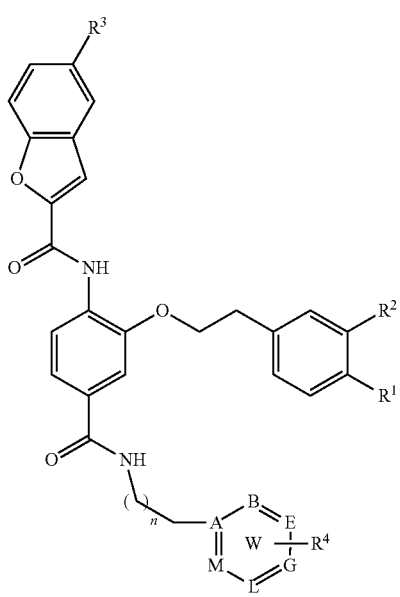

n, $R^1$, $R^2$, $R^3$, and $R^4$ are as defined in Formula I. W is a six-membered aromatic ring structure whose ring atoms: A, B, E, G, L and M are carbon (C) or nitrogen (N) atoms, with no more than two of A, B, E, G, L and M being nitrogen.

Preferably, six-membered aromatic ring structure W is a phenyl ring and $R^4$ is a single substituent that is a meta- or para-substituted halogen, azido, $C_1$-$C_4$ hydrocarbyl, $C_1$-$C_4$ hydrocarbyloxy, or a trifluoromethyl group. In another preference, $R^2$ is hydrido and $R^1$ is hydroxyl.

A preferred compound of Formula III thus corresponds in structure to Formula IV, below, where n, $R^3$, and $R^4$ are as previously defined.
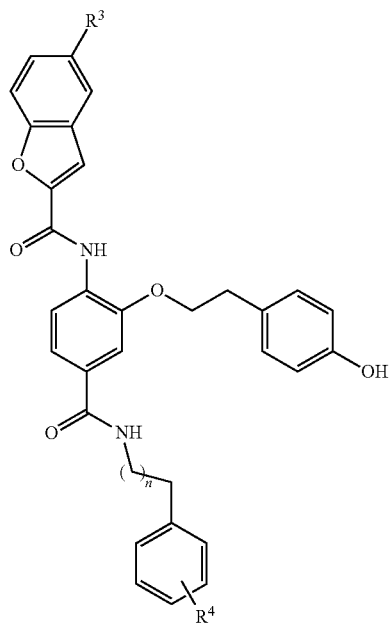
IV
Particularly preferred compounds of Formula II and Formula IV are shown below, where $R^3$ is preferably H (hydrido). Data that illustrate the in vitro efficacy of some of these compounds are shown hereinafter.
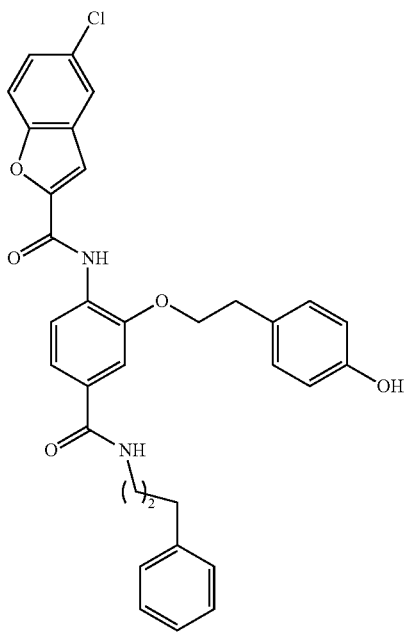
Compound 125-03
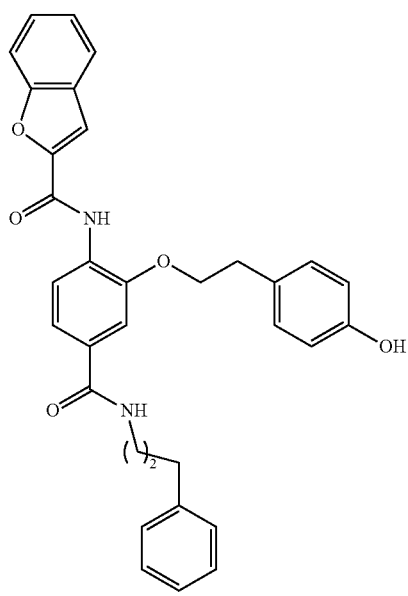
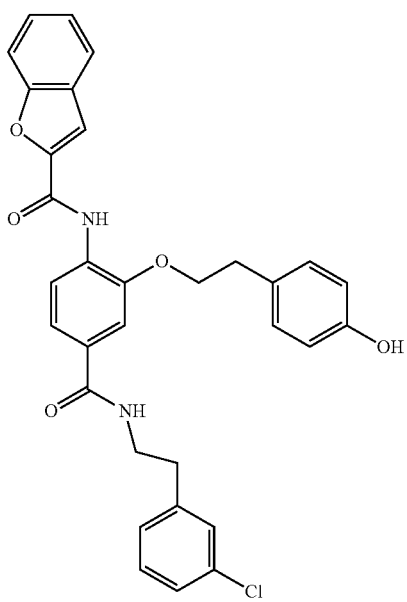

21
-continued
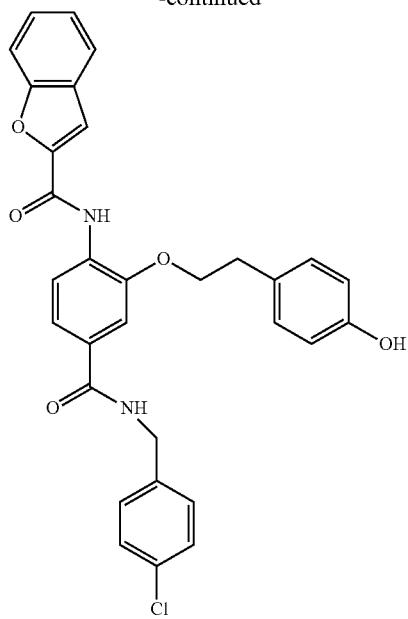
22
-continued
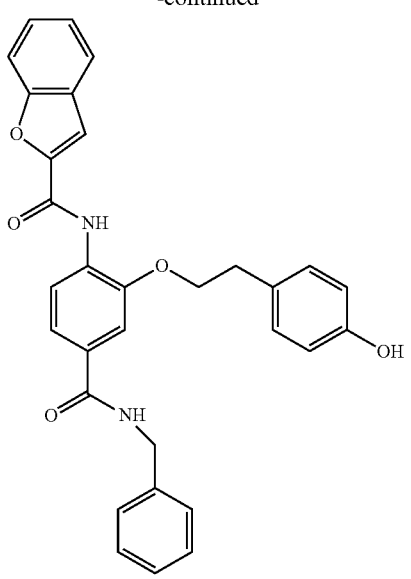
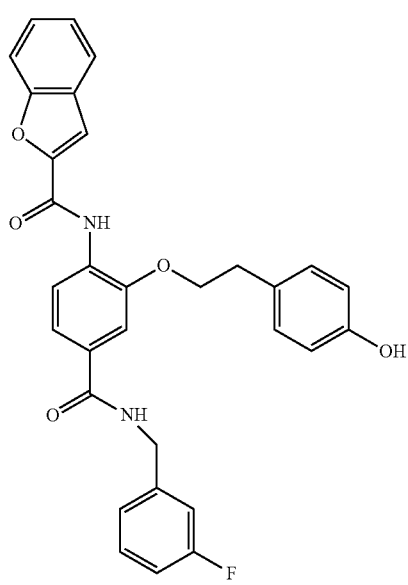
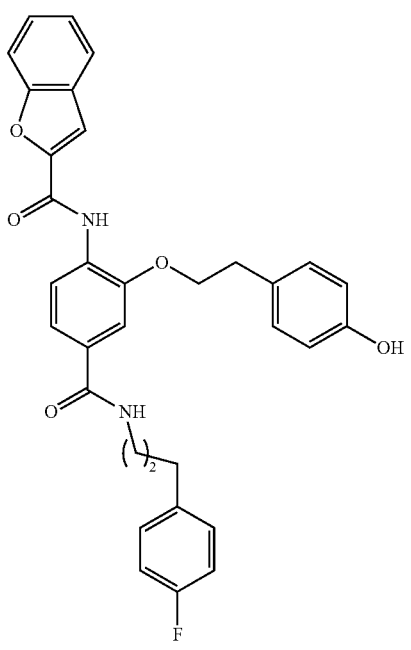

23
-continued
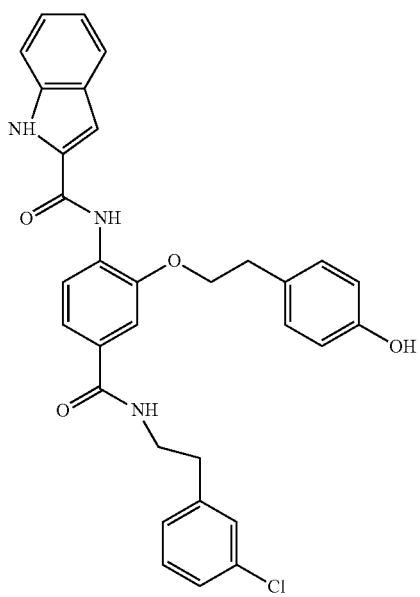
24
-continued
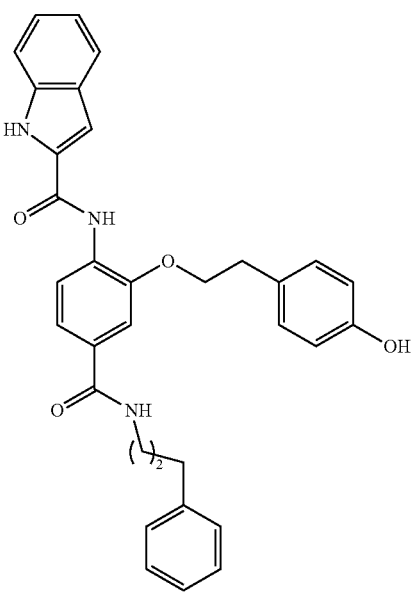
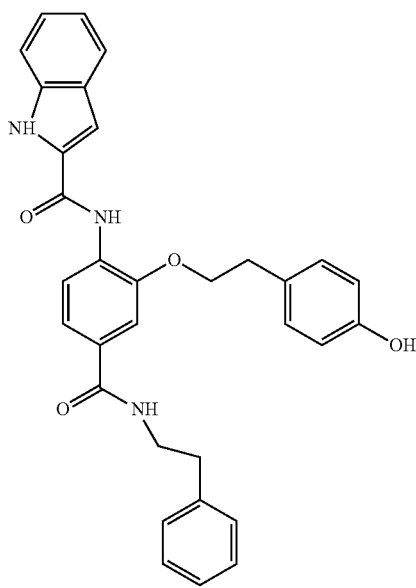
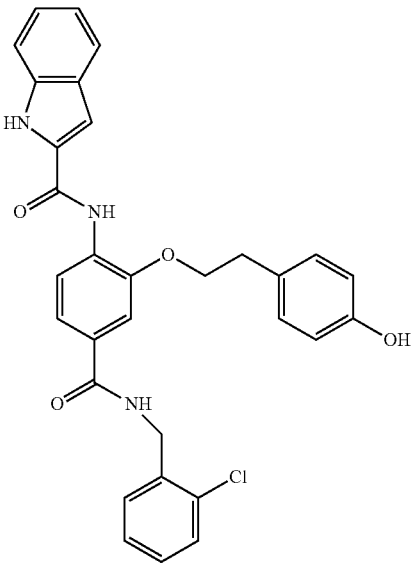

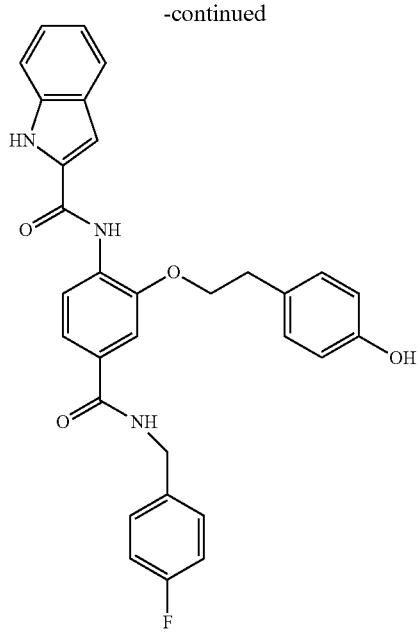
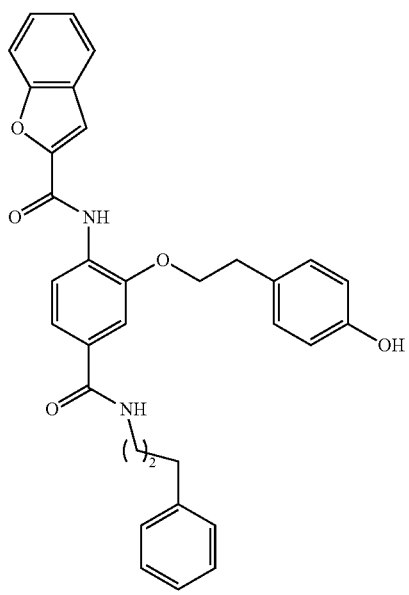
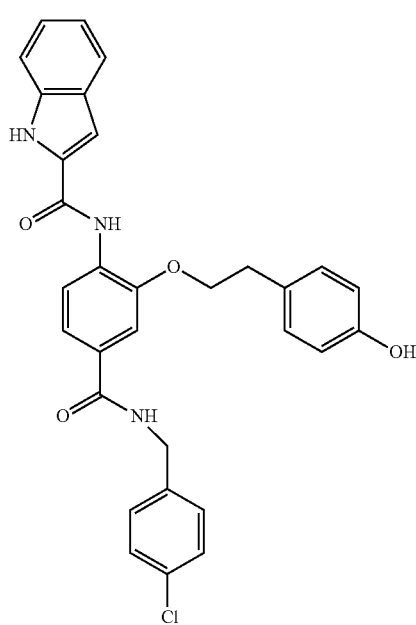
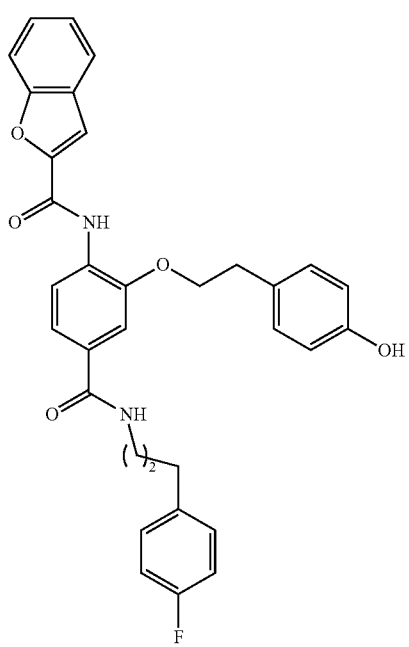
A particularly preferred compound of the above group corresponds in structure to a structural formula shown below, or a pharmaceutically acceptable salt thereof -continued

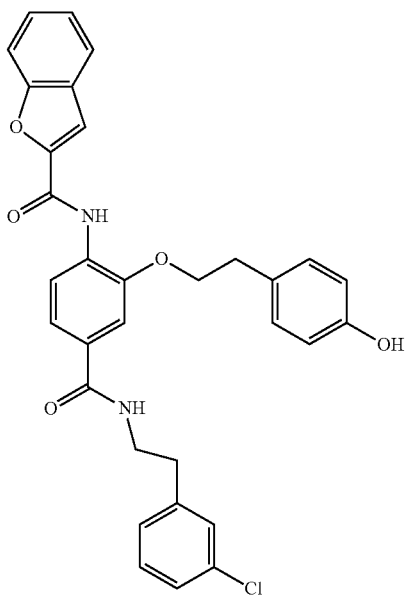

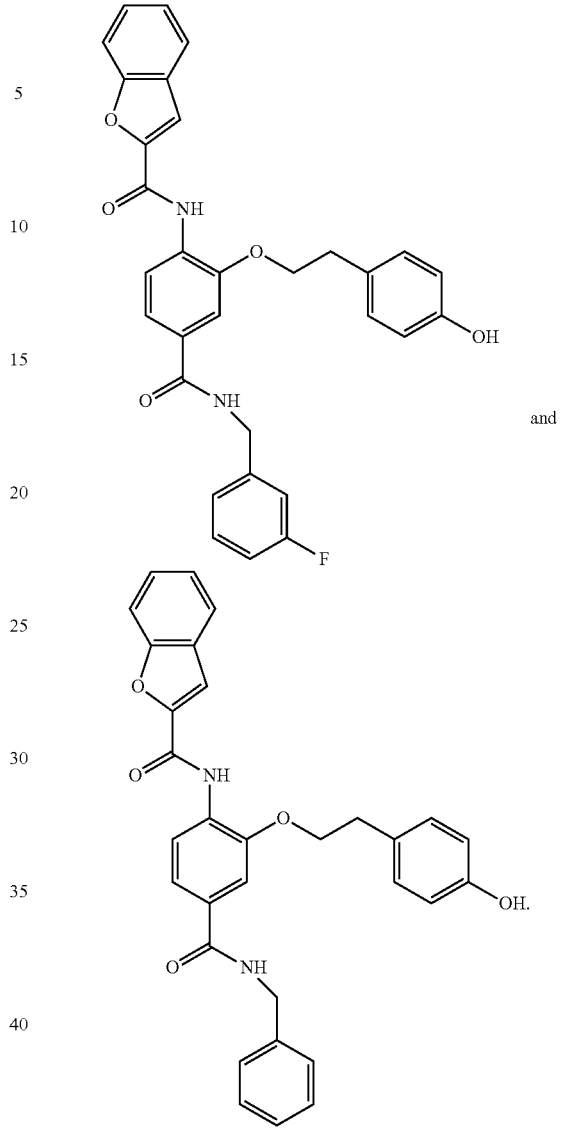

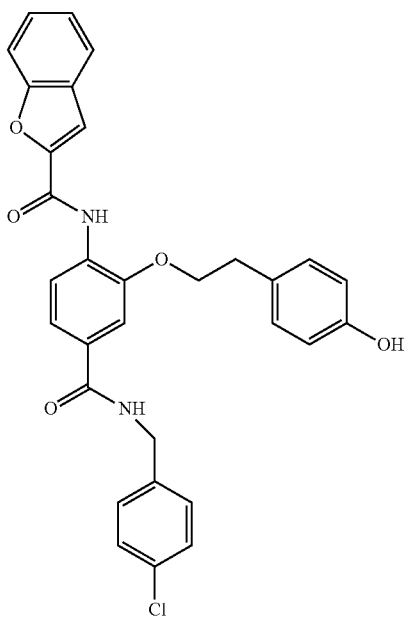

Pharmaceutical Composition and Methods

A contemplated Compound of Formula I can also be used in the manufacture of a medicament (pharmaceutical composition). When so used, a contemplated compound of Formula I is present in an adjuvant-effective amount dissolved or dispersed in a pharmaceutically acceptable diluent (or carrier).

One use for such a composition is as an adjuvant for a vaccine. As such, an improved method of vaccination is contemplated in which a mammal in need of vaccination is administered an effective amount of an immunogen and an effective amount of an adjuvant. Here, the improvement comprises using a Compound of Formula I or its pharmaceutically acceptable salt as the adjuvant.

For example, studies illustrated elsewhere herein show that illustrative Compound 125-03 is a robust in vivo adjuvant that evoked TNF-α production in macrophages from C57BL/6 mice containing disabling germline mutations or knockouts of genes encoding TLRs and downstream signaling proteins (FIG. 1). These studies illustrate that illustrative Compound 125-03 induces TNF-α secretion from macrophages in a manner that is independent of TLRs, including TLR4/MD2.

Figure 3:
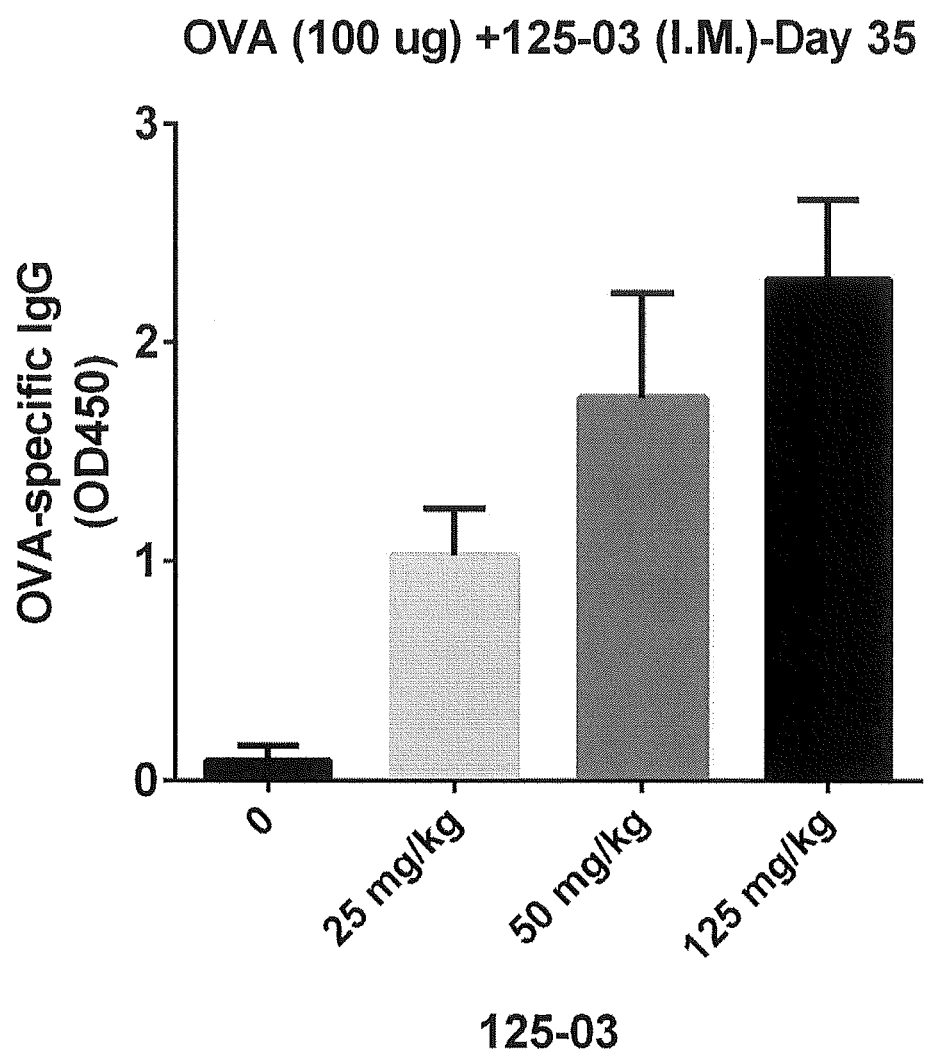
FIG. 3 shows graphs that illustrate ELISA results for the adjuvant effect of Compound 125-03.
Figure 4:
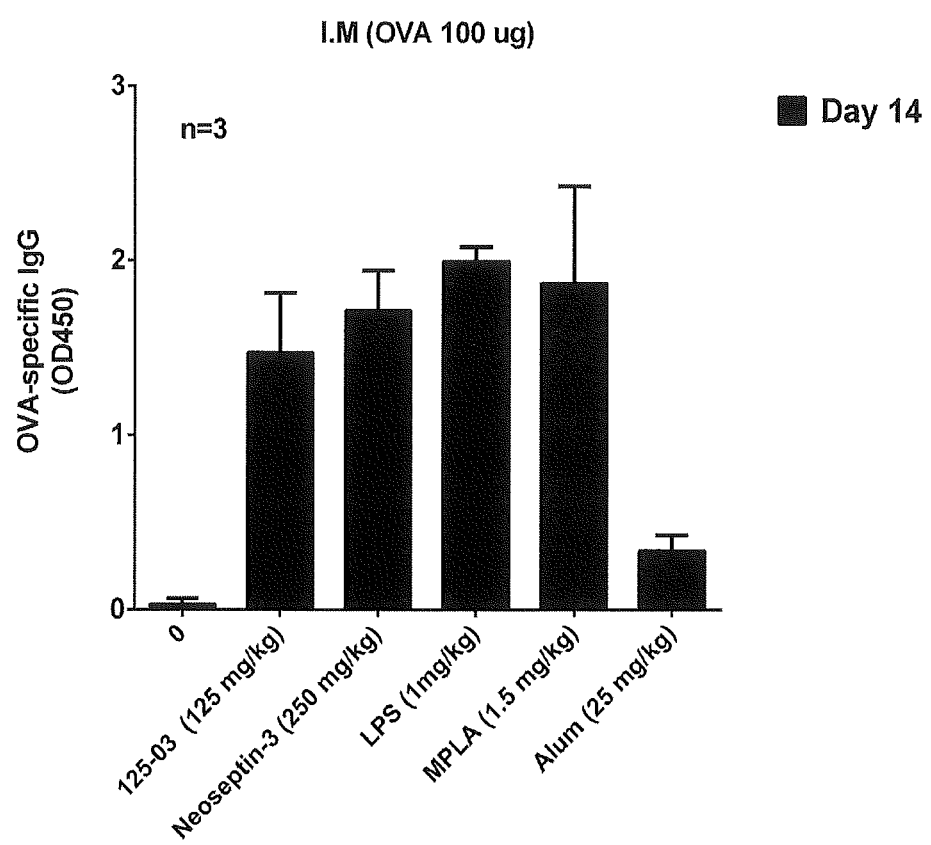

Illustrative Compound 125-03 also induced a sustained IgG immune response in wild type C57BL/6 mice when co-injected with ovalbumin as immunogen by an intramuscular (I.M.) route (FIGS. 3 and 4). That immune response was shown to be dose-dependent (FIG. 3).

In addition, at the maximum doses capable of administration, Compound 125-03 did not display the overt toxicity that is characteristic of LPS administration when used as an adjuvant. Thus, a contemplated Compound of Formula I acts to trigger a response by immune cells (e.g. leukocytes), thereby mimicking the action of LPS, without the toxic result from using LPS as an adjuvant.

Figure 2:
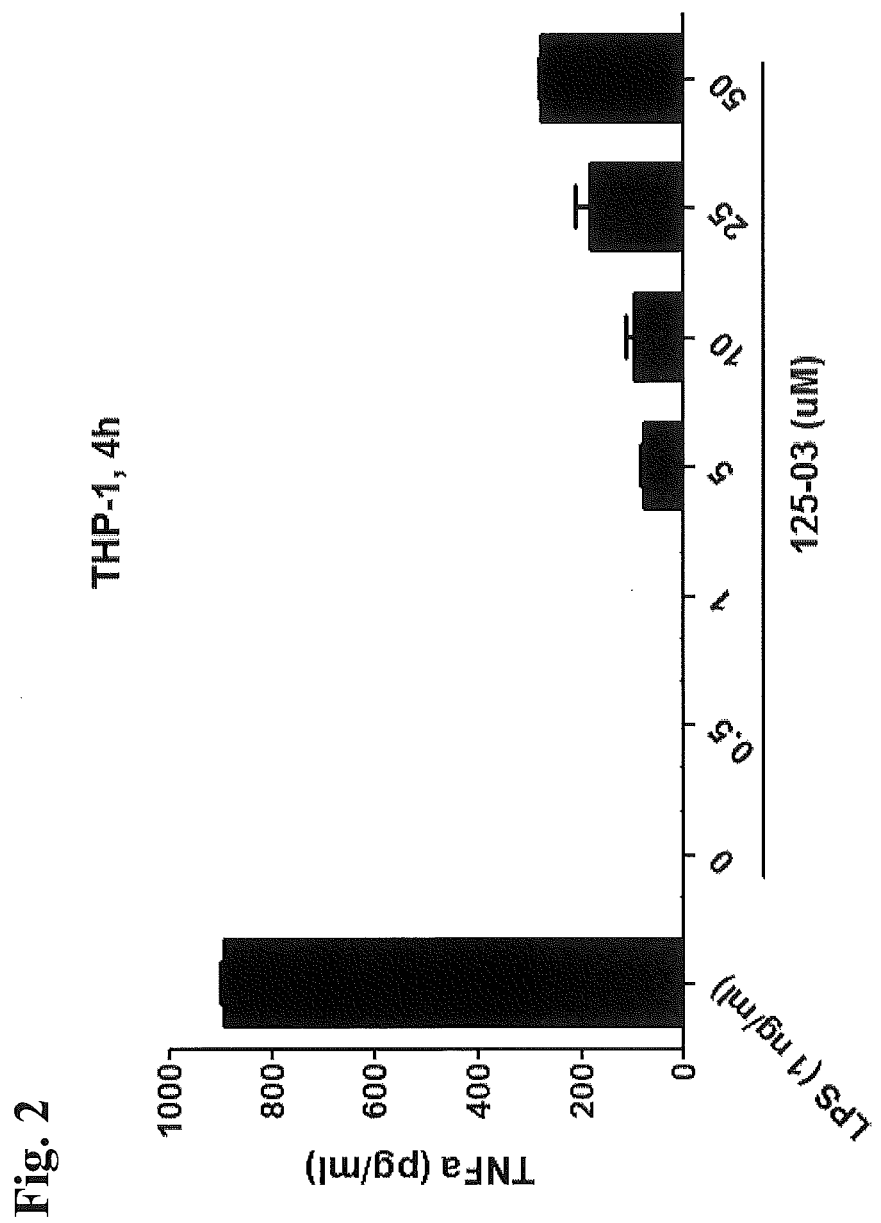
FIG. 2 is a graph that compares the activity of Compound 125-03 and LPS and illustrates that Compound 125-03 exhibits dose dependent activity in human cells, stimulating the release of TNF-alpha from differentiated human THP-1 cells.

In vitro studies in human THP-1 cells illustrated a dose-dependent response to the amount of Compound 125-03 administered to those cells (FIG. 2). Neoceptin-3, a model small molecule adjuvant whose structural formula is shown below, required

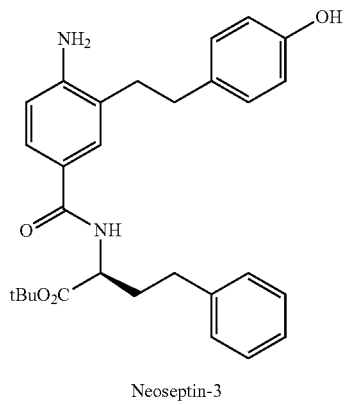 [SMILES: CC(C)(C)OC(=O)[C@H](CCc1ccccc1)NC(=O)c1ccc(N)c(CCc2ccc(O)cc2)c1]

Neoseptin-3 about twice the concentration to produce a similar antibody response at fourteen days. Neoceptin has been shown to be a TLR4-agonist and is not active in human cells.

A contemplated composition also typically contains pharmaceutically acceptable salts, buffers and the like excipients that collectively are referred to as pharmaceutically (or physiologically) acceptable diluents or carriers as compared to those that can be present in a composition that is not intended for pharmaceutical use, as in an in vitro assay.

A compound of the invention can be provided for use by itself, or as a pharmaceutically acceptable salt. For example, a $R^1$ or $R^2$ phenolic hydroxyl group can be acidic and the phenolate ion can be neutralized by a positively charged cation.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate. Salts of the phenylate group include sodium, potassium, magnesium, calcium, aluminum, ammonium, and the many substituted ammonium salts.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vivo and in in vitro assay studies at micromolar amounts. When used in an assay such as an in vitro assay, a contemplated compound is present in the composition in an amount that is sufficient to provide a concentration of about 10 µM to about 100 µM to contact cells to be assayed.

A contemplated pharmaceutical composition contains an effective amount of a Compound of Formula I or a pharmaceutically acceptable salt thereof dissolved or dispersed in a physiologically (pharmaceutically) acceptable carrier. In some embodiments, an adjuvant-effective amount is utilized. Such a composition can be administered to mammalian cells in vitro as in a cell culture to contact those cells, or the cells can be contacted in vivo as in a living, host mammal in need.

When used as a vaccine adjuvant, a Compound of Formula I is preferably administered together with the selected immunogen. Both components are preferably present together in a single composition. However, the two ingredients can be present in separately administered compositions, and those separate compositions can be administered up to about one to about two hours apart. It is preferred when two separate compositions are administered, that they be administered as close together in time as possible.

A Compound of Formula I is present in an adjuvant-effective amount as noted before, whereas the immunogen is present in an immunogen-effective amount that can vary with the immunogen and host animal being vaccinated. These amounts are readily determined by a worker skilled in the art and are illustrated herein for one immunogen.

A Compound of Formula I was illustratively administered in vivo to mice in a weight of adjuvant per kilogram of subject animal at about 10 to about 250 mg/kg, and more usually about 25 to about 125 mg/kg. In usual practice for adjuvants it is known that the amount of adjuvant is not necessarily scalable with the body weight or surface area of the animal host to which it is administered. Rather, an amount of adjuvant used in a small animal can also be useful in a larger animal.

The dose-dependency observed herein is believed to curving toward an asymptote. A skilled worker can readily obtain a suitable concentration for in vivo adjuvant use by starting with the amounts shown herein to be useful. Concentrations useful for assaying in vitro activity are typically those from about 1 to about 100 µM, and more preferably about 5 to about 50 µM.

A contemplated composition is typically administered in vivo to a subject in need thereof a plurality of times within one month, such as daily or weekly, and can be administered over a period of several months to several years. More usually, a contemplated composition is administered a plurality of times over a course of treatment.

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous, intramuscular (which is most preferred), intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a Compound of Formula I or sterile solution of a Compound of Formula I in solvents comprising water, ethanol, or propylene glycol are examples of liquid compositions suitable for parenteral administration. In some aspects, a contemplated Compound of Formula I is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. The amount of a contemplated Compound of Formula I in a solid dosage form is as discussed previously, an amount sufficient to provide a concentration of about 10 mM to about 100 mM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment (a subject or host) and to which a pharmaceutical composition containing a Compound of Formula I is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated Compound of Formula I is administered as an adjuvant along with one or more immunogenic materials as a vaccine. One such composition is illustrated herein in which olvalbumin was used as the immunogen in the vaccination of C57BL/6J mice.

Results

In efforts to improve the TLR4 agonist activity of an initial screening lead, neoseptin-1 (below), measuring the stimulated TNF-alpha release in mouse macrophages, Compound 125-03, used herein as illustrative of the contemplated compounds, emerged as a key compound capable of stimulating the immune response (below). Compound 125-03 was found to be active in stimulating the release of TNF-alpha in both mouse macrophages and in human THP-1 cells differentiated along the macrophage line. It was found to be not only be TLR4 independent, but independent of all other TLRs studied (TLR 2, 3, 4, 6, 7 and 9). [TLRs 1, 2 and 6 have been lost from the mouse genome, and TLRs 11, 12 and 13 have been lost from the human genome. Beutler, *Blood*, 113:1399-1407 (2009).]

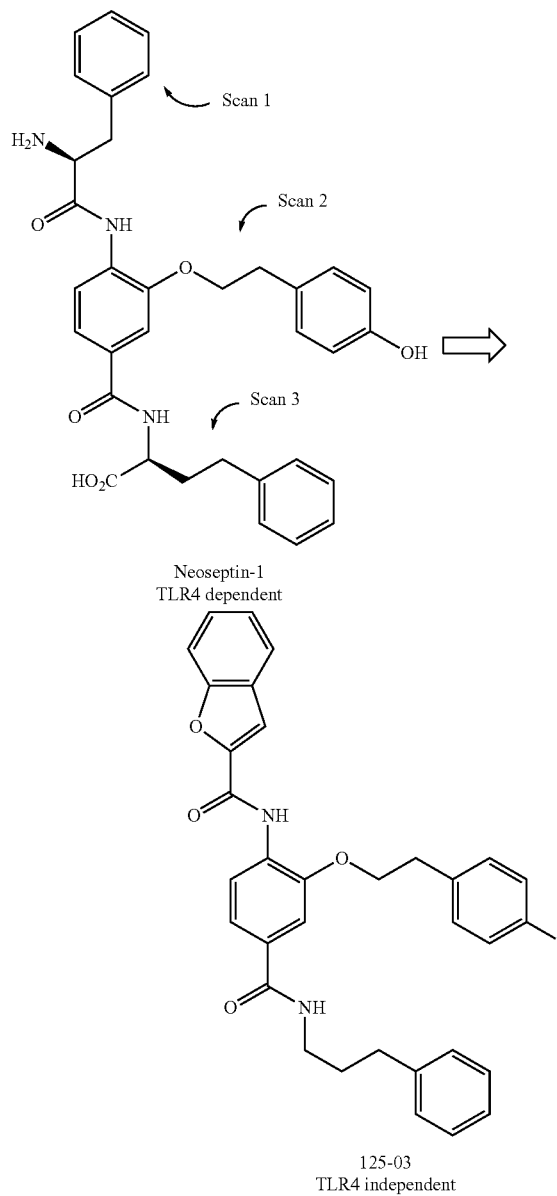

Neoseptin-1
TLR4 dependent 125-03
TLR4 independent

TABLE 1

TNF-α production upon compound treatment (50 μM) of THP-1 cells

| X | R³ | R⁴ | n | TNF-α |
|---|----|----|---|-------|
| O | H | H | 2 | 2000 pg/mL |
| O | Cl | H | 2 | 1057 pg/mL |
| O | H | 3-Cl | 1 | 2477 pg/mL |
| O | H | 4-Cl | 0 | 2112 pg/mL |
| O | H | 3-F | 0 | 1924 pg/mL |
| O | H | 4-F | 2 | 1679 pg/mL |
| O | H | H | 0 | 1679 pg/mL |
| NH | H | 3-Cl | 1 | 1077 pg/mL |
| NH | H | H | 1 | 1185 pg/mL |
| NH | H | H | 2 | 594 pg/mL |
| NH | H | 2-Cl | 0 | 855 pg/mL |
| NH | H | 4-F | 0 | 913 pg/mL |
| NH | H | 4-Cl | 0 | 795 pg/mL |

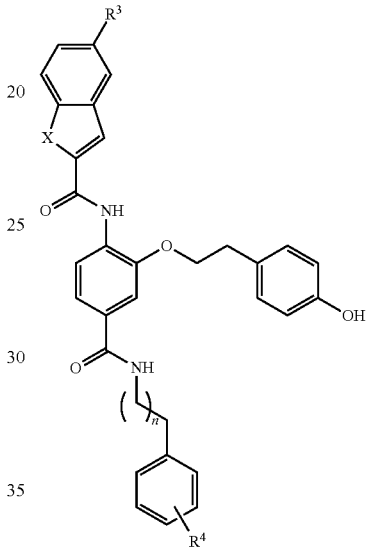

Generalized Structure
125-03
X = O, NH, S, or $CH_2$
n = 0, 1, 2

From Screening Lead to a TLR4-independent Agonist 125-03

Compound 125-03 stimulates TNF-alpha release from both mouse macrophages and differentiated human THP-1 cells and exhibits robust adjuvant activity. Compound 125-03 is in a series distinct from any other compound capable of stimulating the immune response and the original screening lead neoseptin-1. Its SAR has been explored with about 300 analogs independently exploring different areas of the molecule.

These studies have shown that the induced TNF-alpha release in mouse macrophages or differentiated human THP-1 cells requires all the structural elements of the central Tyr side chain (e.g., linker length and phenol OH, and further aryl substitution diminishes or mitigates activity), and it requires the presence and spatial disposition of each terminal aryl side chain where substitution on each is tolerated at most sites. Representative results from contemplated compounds are illustrated in Table 1, below.

The assessment of contemplated compounds such as 125-03 using macrophages from mice containing disabling germline mutations or knockouts of each of the genes encoding the TLRs or the downstream signaling molecules revealed that the induction of TNF-alpha release is independent of all the TLRs including TLR4 and the co-receptors MD-2, CD14, and CD36 (FIG. 1). A contemplated compound does require IRAK4, Sharpin, and IKBKG and, like LPS, it activates the downstream NF-κB, p38 MAPK, and JNK signaling pathways. A photoaffinity cross-linking reagent functionalized for click chemistry pull-down experiments with biotin-N3 was prepared that serves as an antagonist of 125-03, but not LPS, confirming that Compound 125-03 is acting by a distinct mechanism.

Recent mechanistic studies have shown that a mutant of Tab2 (a K63 ubiquitin chain receptor) exhibits an enhanced response to Compound 125-03. Also, knockdown of Cyld, a deubiqiutinase in the TLR signaling pathway, exhibits an enhanced response to Compound 125-03. Further, in vitro assay results suggest that Compound 125-03 directly inhibits Cyld activity. In addition, Compound 125-03 also markedly increased responses to TLR ligands including neoseptin-3. These results imply, but do not fully establish Cyld is the target for Compound 125-03 and the other compounds of Formula I.

Illustrative Compound 125-03 displays robust, dose-dependent activity for stimulating TNF-alpha release (FIG. 2) and is active and effective in both mouse macrophages and differentiated human THP-1 cells. It displays potent, dose dependent, and efficacious adjuvant activity in vivo (FIG. 3) and is more effective than alum at the concentrations used (FIG. 4).

Compound 125-03 is a chemically attractive small molecule amenable to extensive chemical modification that activates the immune response and displays an exquisitely selective SAR.

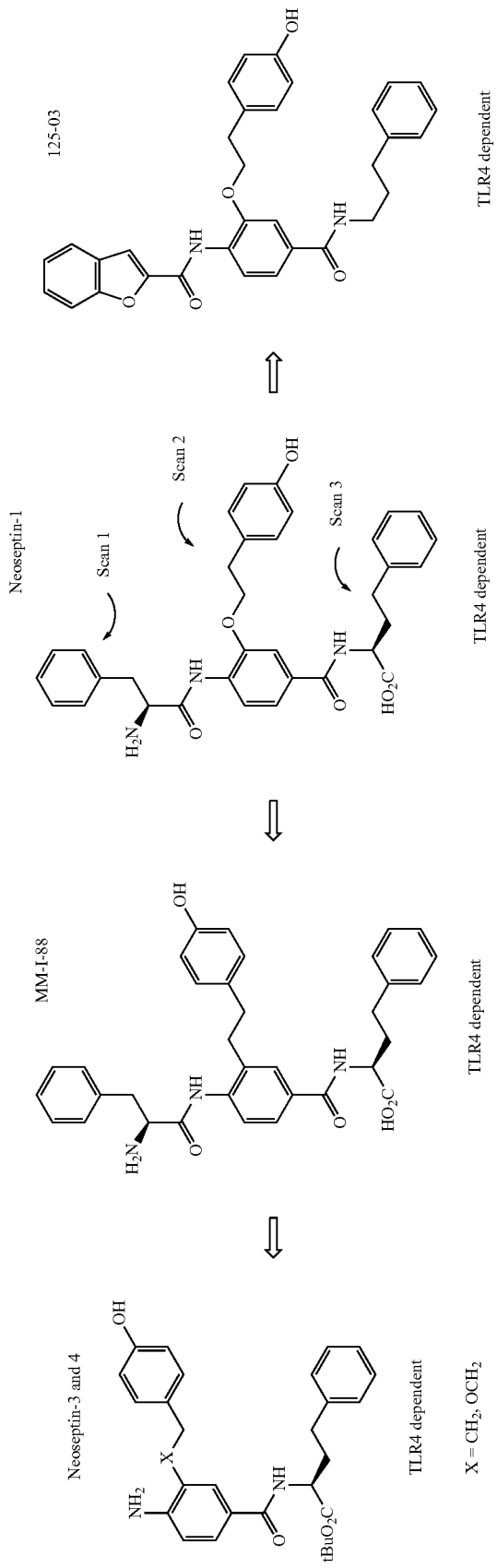

The activity of the initial screening lead, neoseptin-1, below, was optimized

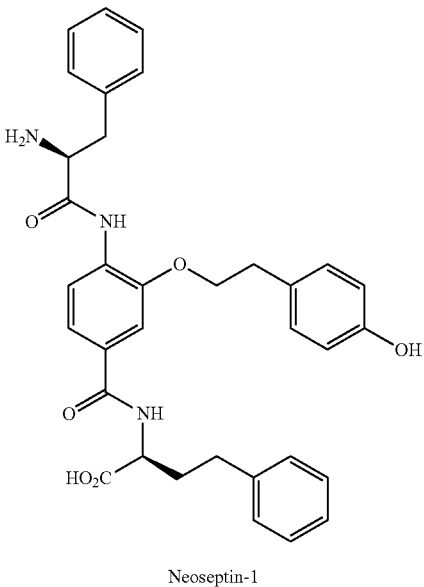 [SMILES: N[C@@H](Cc1ccccc1)C(=O)Nc1ccc(C(=O)N[C@@H](CCc2ccccc2)C(=O)O)cc1OCCc1ccc(O)cc1]

Neoseptin-1 via preparation of about 850 compounds, probing the two end portions of the structure.

Upon exploring the central region of neoseptin-1 (80 compounds), a significant enhancement in TLR4 agonist efficacy was discovered with Compound MM-1-88, below, where a single atom change in

MM-I-88

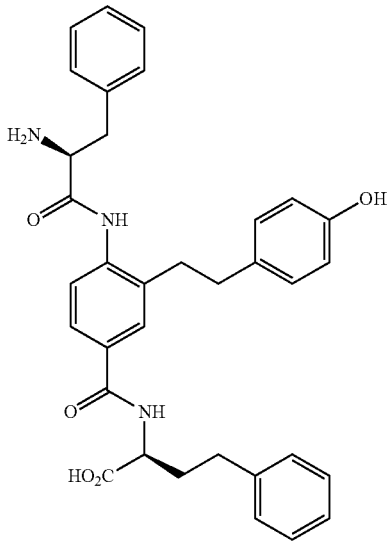

neoseptin-1 (removal of a single oxygen atom) provided the increased efficacy. Nearly all other changes to this region of the molecule led to a complete loss in activity. Further optimization led to additional simplifying structural modifications and two proved to be even more efficacious TLR4-dependent agonists (named neoseptin-3 and neoseptin-4), nearly matching the efficacy of LPS.

Induced TNF-α production was established with the use of macrophages from mice bearing germline genetic defects or knockouts of each of the genes encoding the TLRs or their downstream signaling molecules uniquely available in the laboratories of Professor Bruce Beutler, (University of Texas Southwestern Medical Center, Dallas, Tex.). See, (a) mutagenetix.utsouthwestern.edu.; (b) Arnold et al., (2012) ENU-induced phenovariance in mice: Inferences from 587 mutations. *BMC Res. Notes.* 5, 577-0500-5-577.

Compound Preparation

A contemplated Compound of Formula I can be readily prepared using standard organic chemistry procedures. Illustrative syntheses of Compound 125-03 is shown as a model for the syntheses of other molecules described herein. The compounds whose in vitro induced TNF-alpha release results from human THP-1 cells were prepared in a manner analogous to the preparation of Compound 125-03 as illustrated in Scheme 1 hereinafter.

4-Nitro-3-(4-(triisopropylsiloxy)-phenethoxy)-benzoic acid (I)

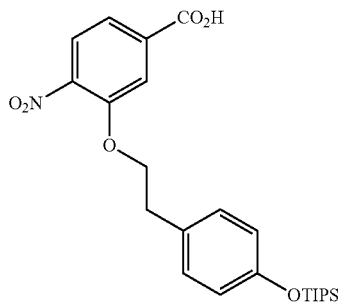

Sodium hydride (500 mg, approx. 2.4 equiv, 60% suspension in mineral oil) was suspended in anhydrous THF (25 mL) and cooled to 0° C. 2-(4-(Triisopropylsiloxy)phenyl)ethanol [Shah et al., *Org. Biomol. Chem.* 2008, 6, 2168-2172] (1.50 g, 5.09 mmol) was added dropwise to the vigorously stirring suspension. The cold bath was removed, and the mixture was stirred for 20 minutes. After cooling to 0° C., 3-fluoro-4-nitrobenzoic acid (915 mg, 4.85 mmol) was added slowly as a solution in anhydrous DMF (5 mL). The cold bath was removed again and the mixture was stirred for 3.5 hours at room temperature. The reaction was quenched with 2 N HCl (75 mL) and diluted with EtOAc (75 mL). The aqueous phase was extracted with EtOAc (50 mL), and the organic phase dried over $Na_2SO_4$, decanted and concentrated in vacuo. The product was crystallized from hexanes to afford 1.40 g (63%) of I as an off-white solid. $^1$H NMR (500 MHz, DMSO-$d_6$) δ 7.99 (d, J=8.3 Hz, 1H), 7.81 (d, J=1.6 Hz, 1H), 7.68 (dd, J=8.4, 1.5 Hz, 1H), 7.23 (d, J=8.5 Hz, 2H), 6.84 (d, J=8.5 Hz, 2H), 4.46 (t, J=6.7 Hz, 2H), 3.03 (t, J=6.6 Hz, 2H), 1.33-1.23 (m, 3H), 1.11 (d, J=7.4 Hz, 18H).

Methyl 4-nitro-3-(4-(triisopropylsiloxy)-phenethoxy)-benzoate (II)

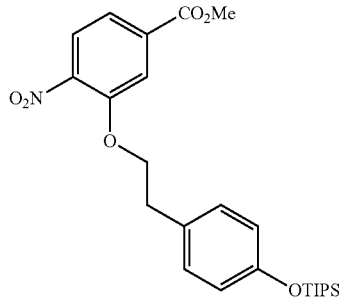

Carboxylic acid I (1.00 g, 2.18 mmol) was dissolved in MeOH (10 mL). (Trimethylsilyl)-diazomethane (1.63 mL, 1.50 equiv, 2 M solution in hexanes) was added dropwise, with concomitant evolution of $N_2$ gas. After 2 hours, AcOH (approx. 0.5 mL, glacial) was added slowly until gas evolution ceased. Reaction solvent was removed in vacuo and the residue was redissolved in EtOAc (30 mL) and washed with sat. $NaHCO_3$ (25 mL). The organic phase was dried over $Na_2SO_4$, filtered and concentrated to afford 973 mg (94%) of methyl ester II, which was used without further purification. $^1$H NMR (400 MHz, $CDCl_3$) δ 7.98 (d, J=8.3 Hz, 1H), 7.87 (d, J=1.6 Hz, 1H), 7.83 (dd, J=8.4, 1.5 Hz, 1H), 7.30 (d, J=8.4 Hz, 2H), 7.00 (d, J=8.4 Hz, 2H), 4.47 (t, J=6.9 Hz, 2H), 4.11 (s, 3H), 3.25 (t, J=6.9 Hz, 2H), 1.48-1.35 (m, 3H), 1.26 (d, J=7.3 Hz, 18H).

Methyl 4-amino-3-(4-(triisopropylsiloxy)-phenethoxy)-benzoate (III)

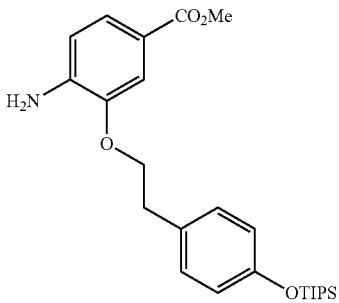

Methyl ester II (973 mg, 2.05 mmol) was dissolved in acetone (25 mL). Zinc nanopowder (2.02 g, 30.8 mmol, 15 equiv) was suspended in the reaction solvent, and the mixture was cooled to 0° C. With vigorous stirring, sat. $NH_4Cl$ (6 mL) was added dropwise. After 1 hour, the heterogeneous mixture was filtered through Celite® to remove the Zn salts, and the filtrate was diluted with EtOAc (50 mL) and washed with $H_2O$ (50 mL). The organic phase was dried over $Na_2SO_4$, decanted and concentrated to give 905 mg (99%) of aniline III. $^1$H NMR (500 MHz, DMSO-$d_6$) δ 7.37 (dd, J=8.2, 1.8 Hz, 1H), 7.28 (d, J=1.9 Hz, 1H), 7.22 (d, J=8.4 Hz, 2H), 6.79 (d, J=8.5 Hz, 2H), 6.64 (d, J=8.2 Hz, 1H), 5.49 (s, 2H), 4.13 (t, J=6.7 Hz, 2H), 3.73 (s, 3H), 2.99 (t, J=6.7 Hz, 2H), 1.27-1.17 (m, 3H), 1.05 (d, J=7.4 Hz, 18H).

Methyl 4-(benzofuran-2-carboxamido)-3-(4-(triisopropylsiloxy)phenethoxy)benzoate (IV)

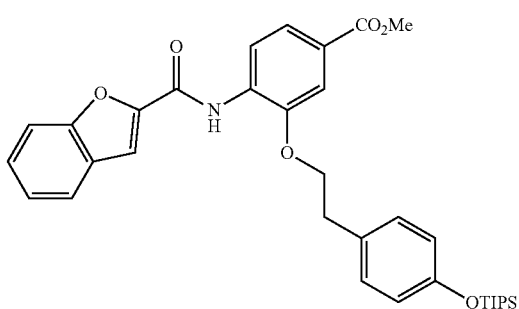

Benzofuran-2-carboxylic acid (268 mg, 1.65 mmol) was combined with aniline III (733 mg, 1.65 mmol) in DMF (8.0 mL) in a 20 mL scintillation vial. 1-Hydroxy-7-azabenzotriazole (HOAt; 250 mg, 1.82 mmol), EDCI.HCl (333 mg, 1.73 mmol), and 2,6-lutidine (0.965 mL, 8.26 mmol) were added. After stirring at room temperature for 48 hours, the reaction mixture was poured into aqueous 0.1 N HCl (50 mL). The aqueous layer was extracted with EtOAc (2×50 mL). The combined extract was washed with saturated aqueous $NaHCO_3$ (30 mL) and saturated aqueous NaCl (30 mL), dried over $Na_2SO_4$, filtered and evaporated in vacuo. Flash chromatography ($SiO_2$, 20% EtOAc/hexanes) yielded 762 mg (78%) of the coupled product IV. $^1$H NMR (500 MHz, $CDCl_3$) δ 9.14 (s, 1H), 8.62 (d, J=8.5 Hz, 1H), 7.76-7.70 (m, 2H), 7.66-7.63 (m, 1H), 7.59 (dd, J=2.8, 1.4 Hz, 2H), 7.50 (ddd, J=8.4, 7.2, 1.3 Hz, 1H), 7.36 (ddd, J=7.9, 7.2, 0.9 Hz, 1H), 7.29 (d, J=8.4 Hz, 2H), 6.77 (d, J=8.4 Hz, 2H), 4.37 (t, J=6.2 Hz, 2H), 3.91 (s, 3H), 3.20 (t, J=6.2 Hz, 2H), 1.13-1.02 (m, 3H), 0.97 (d, J=7.1 Hz, 18H).

4-(Benzofuran-2-carboxamido)-3-(4-hydroxyphenethoxy)benzoic acid (V)

N-(2-(4-Hydroxyphenethoxy)-4-((3-phenylpropyl)carbamoyl)phenyl)benzofuran-2-carboxamide (125-03)

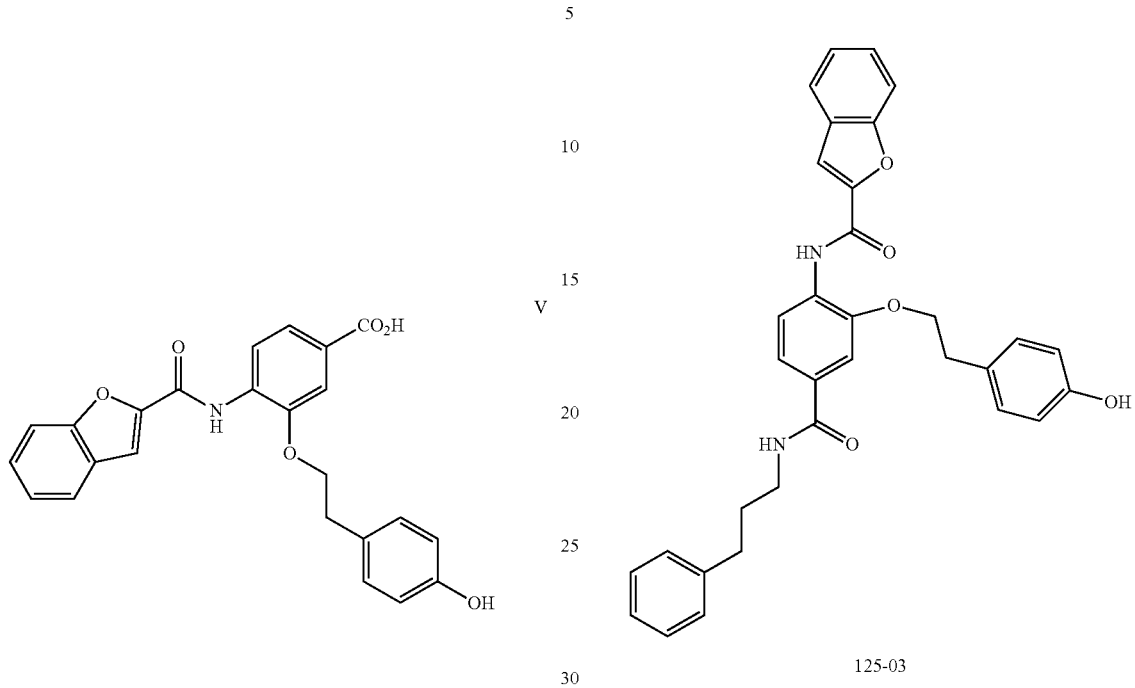

Methyl ester IV (762 mg, 1.30 mmol) was dissolved in a mixture of THF/MeOH/H$_2$O (9 mL, 3 mL, 3 mL, respectively). LiOH.H$_2$O (544 mg, 13.0 mmol, 10 equiv) was added portionwise over 10 minutes. After 4 hours, the reaction mixture was concentrated under N$_2$ stream to ⅕ the original volume, and H$_2$O (150 mL) was added to form a milky solution. The solution was washed once with Et$_2$O (25 mL) and the ethereal layer was separated and discarded. The remaining aqueous solution was acidified with 2 N HCl until pH about 2, upon which the product carboxylic acid began to precipitate. The precipitate was redissolved in EtOAc (100 mL), and the aqueous phase was extracted with EtOAc (2×50 mL). The combined organic phases were dried over Na$_2$SO$_4$, filtered and concentrated to reveal 496 mg (92%) of carboxylic acid V. $^1$H NMR (500 MHz, DMSO-d$_6$) δ 9.29 (s, 1H), 9.13 (d, J=2.1 Hz, 1H), 8.32 (d, J=8.3 Hz, 1H), 7.86 (d, J=7.4 Hz, 1H), 7.78 (d, J=8.4 Hz, 1H), 7.76 (d, J=1.1 Hz, 1H), 7.66-7.55 (m, 3H), 7.43 (t, J=7.8 Hz, 1H), 7.26 (d, J=8.4 Hz, 2H), 6.60 (d, J=8.4 Hz, 2H), 4.34 (t, J=6.0 Hz, 2H), 3.07 (t, J=6.1 Hz, 2H).

Carboxylic acid V (377 mg, 0.903 mmol) was combined with 3-phenyl-1-propylamine (122 mg, 0.903 mmol) in DMF (4.5 mL). HOAt (135 mg, 0.994 mmol), EDCI.HCl (182 mg, 0.948 mmol), and 2,6-lutidine (0.525 mL, 4.52 mmol) were added. After stirring at room temperature for 12 hours, the reaction mixture was poured into aqueous 1 N HCl (20 mL). Precipitated product at this stage was recovered by filtration. The aqueous layer was extracted with EtOAc (2×40 mL). The combined extract was washed with saturated aqueous NaHCO$_3$ (20 mL) and saturated aqueous NaCl, dried over Na$_2$SO$_4$, filtered and concentrated in vacuo. The resulting residue was redissolved in CH$_2$Cl$_2$ (50 mL) with sonication. Chilled hexanes (1-2 mL) was added dropwise to the cloudy solution, and the remaining product was isolated by filtration, to give 376 mg (78%) of 125-03. $^1$H NMR (500 MHz, DMSO-d$_6$) δ 9.28 (s, 1H), 9.15 (s, 1H), 8.46 (t, J=5.7 Hz, 1H), 8.23 (d, J=8.3 Hz, 1H), 7.86 (d, J=7.6 Hz, 1H), 7.78 (d, J=8.4 Hz, 1H), 7.75 (s, 1H), 7.61-7.54 (m, 2H), 7.52 (dd, J=8.4, 1.8 Hz, 1H), 7.42 (t, J=7.6 Hz, 1H), 7.32-7.20 (m, 6H), 7.18 (m, 1H), 6.61 (d, J=8.4 Hz, 2H), 4.32 (t, J=6.3 Hz, 2H), 3.32-3.24 (m, 2H), 3.07 (t, J=6.2 Hz, 2H), 2.64 (t, J=7.7 Hz, 2H), 1.88-1.79 (m, 2H); IR (neat) ν$_{max}$ 3279, 1656, 1622, 1444, 1305, 1274 cm$^{-1}$; LRMS (ESI-TOF) m/z 535.2 (calcd for C$_{33}$H$_{31}$N$_2$O$_5$ requires 535.2); HRMS (ESI-TOF) m/z calcd for C$_{33}$H$_{30}$N$_2$O$_5$ [M+H]$^+$ 535.2227. found 535.2229.

The exemplary compounds utilized in Table 1 were prepared in a manner analogous to that used for the preparation of Compound 125-03 discussed above that started with Compound III. That synthetic process is shown illustratively in Scheme 1, below.

Scheme 1
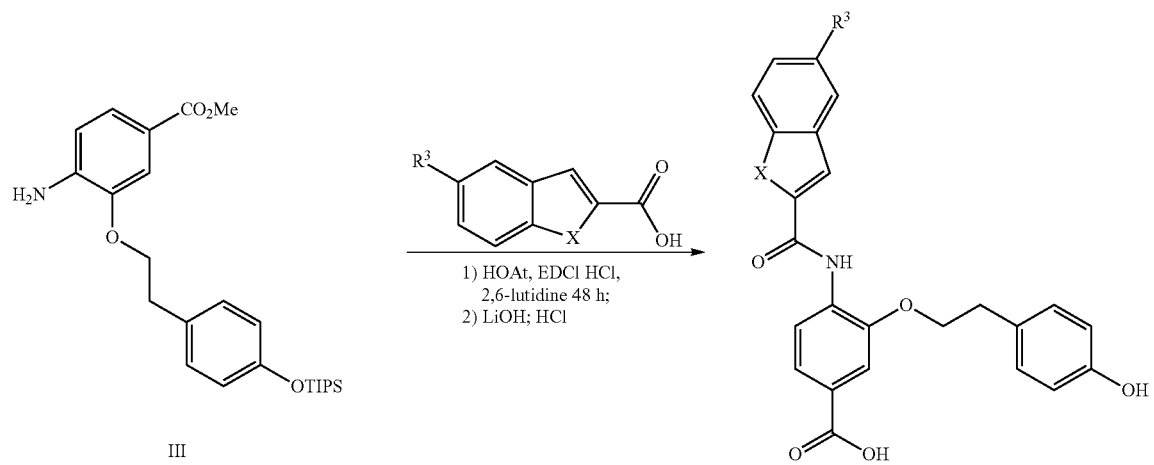
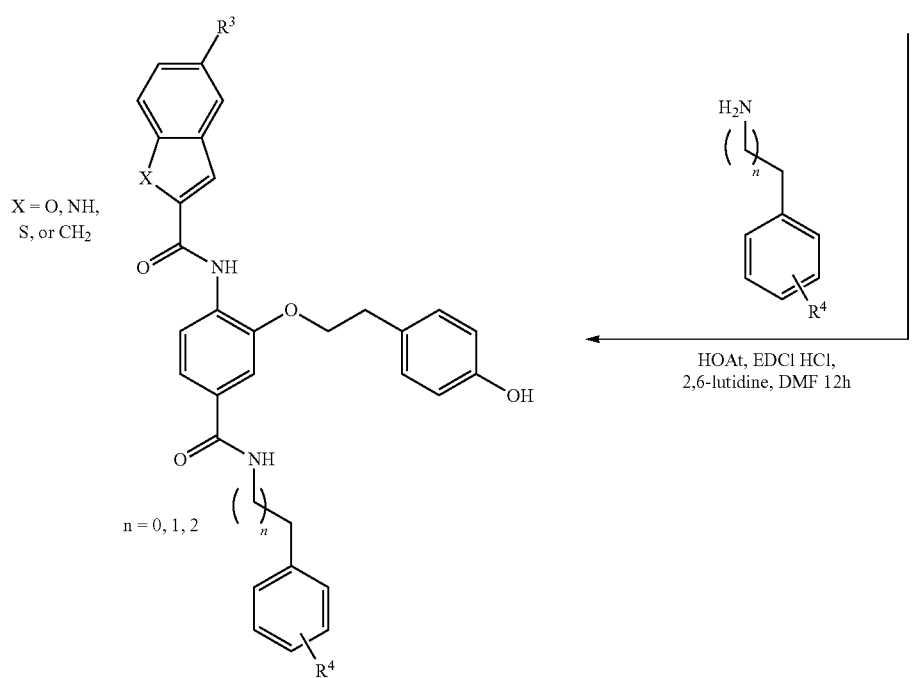
X = O, NH, S, or CH$_2$
n = 0, 1, 2
R$^3$ = H or Cl
R$^4$ = H, 3-Cl, 4-Cl
3-F, 4-F, 2-Cl An alternative synthesis for these compounds is set out in Scheme 2, below.
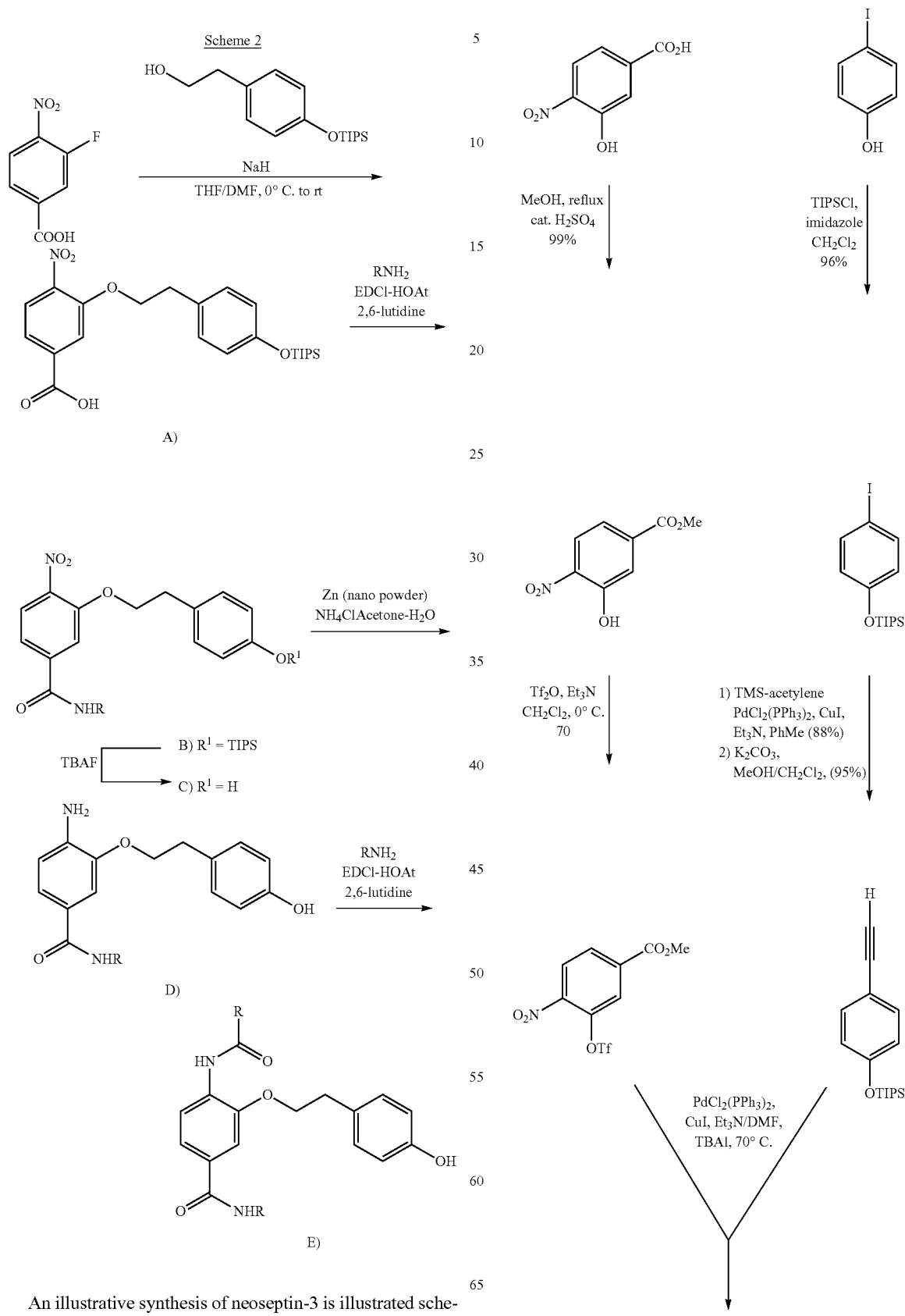
An illustrative synthesis of neoseptin-3 is illustrated schematically below in Schemes 3A and 3B.

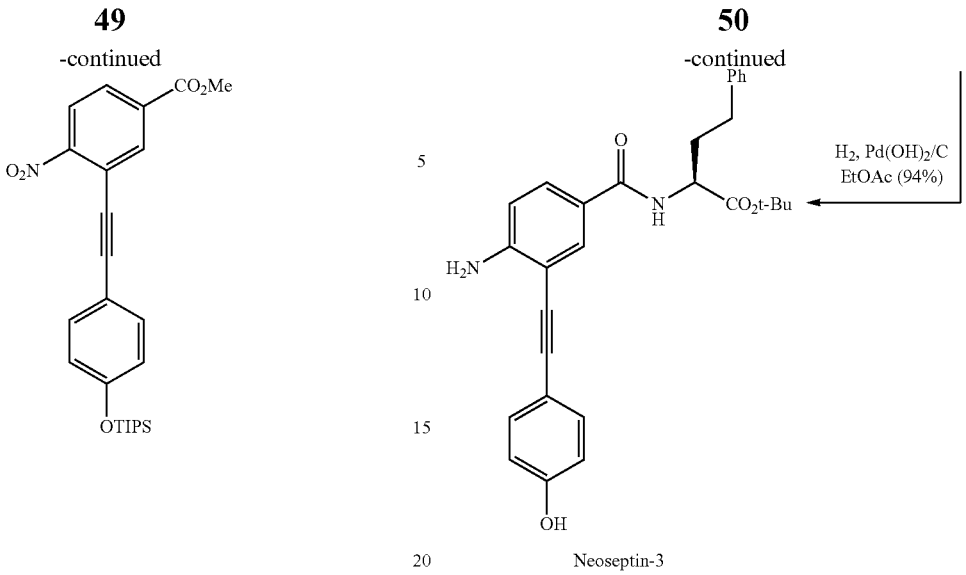

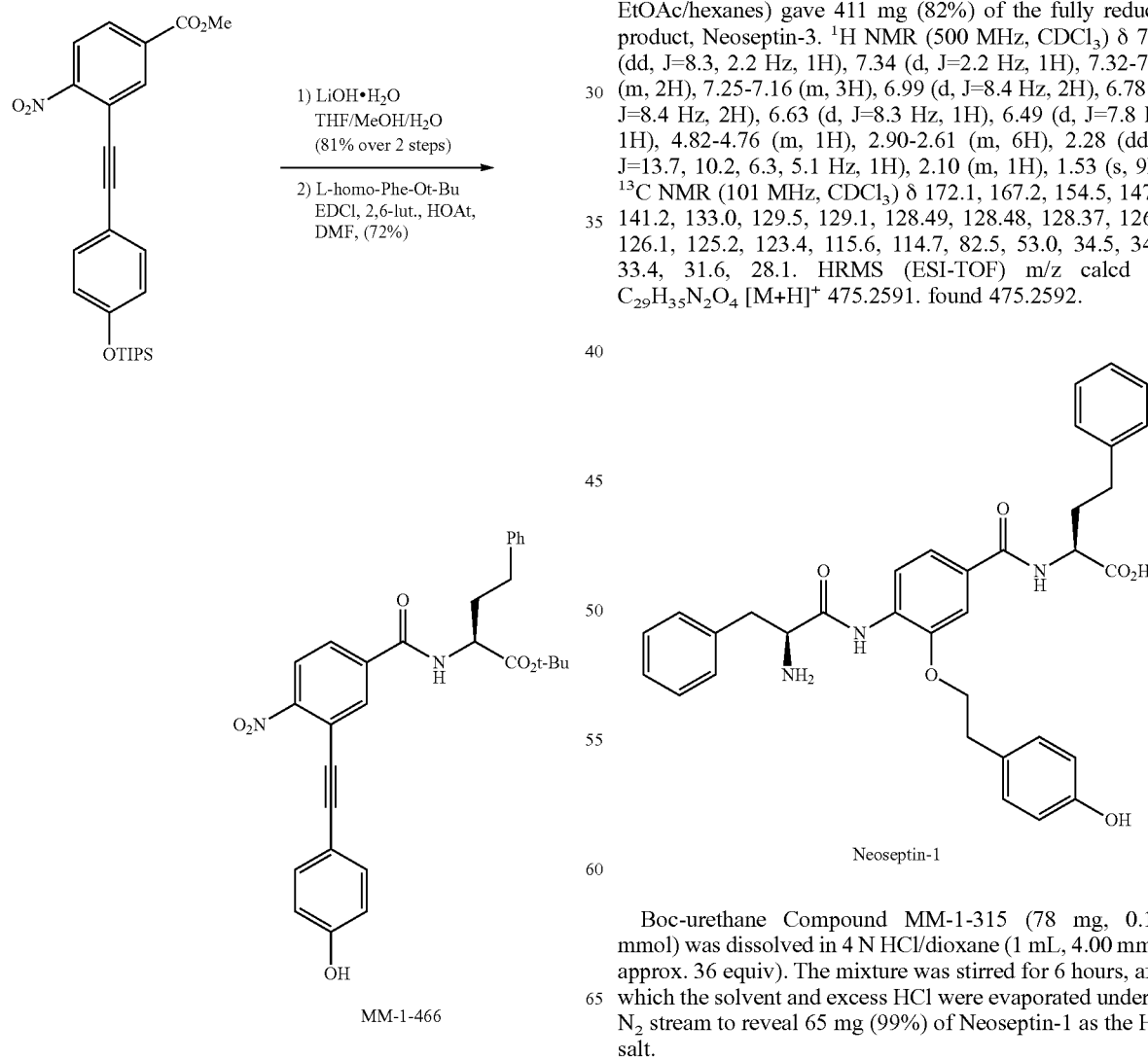

Neoseptin-3 The general procedure for nitroaryl alkyne reduction was followed: Nitroalkyne MM-1-466 (530 mg, 1.06 mmol), EtOAc (10 mL), Pearlman's catalyst (250 mg) were employed. Flash chromatography (SiO$_2$, 30 to 50% EtOAc/hexanes) gave 411 mg (82%) of the fully reduced product, Neoseptin-3. $^1$H NMR (500 MHz, CDCl$_3$) δ 7.44 (dd, J=8.3, 2.2 Hz, 1H), 7.34 (d, J=2.2 Hz, 1H), 7.32-7.28 (m, 2H), 7.25-7.16 (m, 3H), 6.99 (d, J=8.4 Hz, 2H), 6.78 (d, J=8.4 Hz, 2H), 6.63 (d, J=8.3 Hz, 1H), 6.49 (d, J=7.8 Hz, 1H), 4.82-4.76 (m, 1H), 2.90-2.61 (m, 6H), 2.28 (dddd, J=13.7, 10.2, 6.3, 5.1 Hz, 1H), 2.10 (m, 1H), 1.53 (s, 9H). $^{13}$C NMR (101 MHz, CDCl$_3$) δ 172.1, 167.2, 154.5, 147.8, 141.2, 133.0, 129.5, 129.1, 128.49, 128.48, 128.37, 126.3, 126.1, 125.2, 123.4, 115.6, 114.7, 82.5, 53.0, 34.5, 34.2, 33.4, 31.6, 28.1. HRMS (ESI-TOF) m/z calcd for C$_{29}$H$_{35}$N$_2$O$_4$ [M+H]$^+$ 475.2591. found 475.2592.

Boc-urethane Compound MM-1-315 (78 mg, 0.112 mmol) was dissolved in 4 N HCl/dioxane (1 mL, 4.00 mmol, approx. 36 equiv). The mixture was stirred for 6 hours, after which the solvent and excess HCl were evaporated under an N$_2$ stream to reveal 65 mg (99%) of Neoseptin-1 as the HCl salt.

Hz, 2H), 4.55 (q, J=6.1 Hz, 1H), 4.50-4.45 (m, 1H), 4.15 (t, J=6.4 Hz, 2H), 3.00 (t, J=6.4 Hz, 2H), 2.70-2.60 (m, 4H), 2.35-2.25 (m, 1H), 2.15-2.00 (m, 1H), 1.50 (s, 9H), 1.45 (s, 9H); MS-ESI (m/z) calcd for $[C_{43}H_{51}N_3O_8+H]^+$ 737.3; found: 738.3.

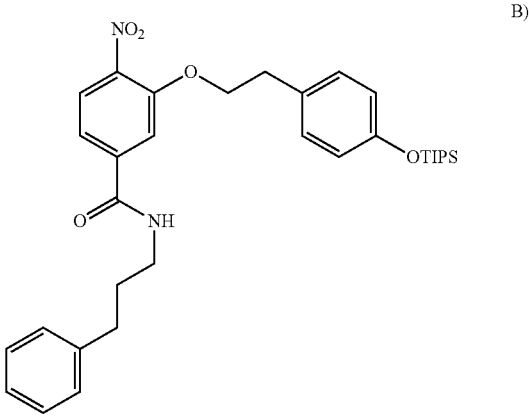

B)

Compound B) was prepared following the steps laid out in Scheme 2. Thus, carboxylic acid Compound A) (120 mg, 0.261 mmol), 3-phenylpropylamine (35 mg, 0.261 mmol, 1 equiv), 2,6-lutidine (0.084 mL, 0.783 mmol, 3 equiv), HOAt (43 mg, 0.313 mmol, 1.2 equiv) and EDCI.HCl (60 mg, 0.313 mmol, 1.2 equiv) were utilized. Flash chromatography (20% EtOAc/hexanes) gave 119 mg (79%) of Compound B).

Illustrative mass spectral data for several compounds of Formula I and related compounds are shown below. In the depictions below, $R_1$ and $R_2$ are different from the previously discussed $R^1$ and $R^2$ substituents of Formula I and $R^1$ and $R^2$ of the claims.

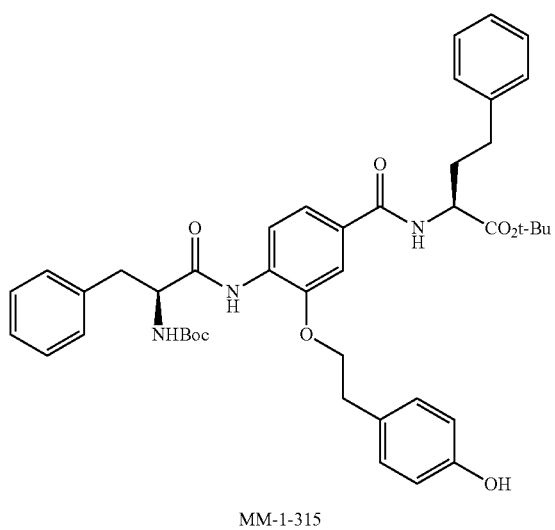 [SMILES: CC(C)(C)OC(=O)N[C@@H](Cc1ccccc1)C(=O)Nc1ccc(C(=O)N[C@@H](CCc2ccccc2)C(=O)OC(C)(C)C)cc1OCCc1ccc(O)cc1]

MM-1-315

TIPS-Neoseptin-4 (200 mg, 0.309 mmol), HOAt (46 mg, 0.340 mmol, 1.1 equiv) and Boc-Phe-OH (82 mg,

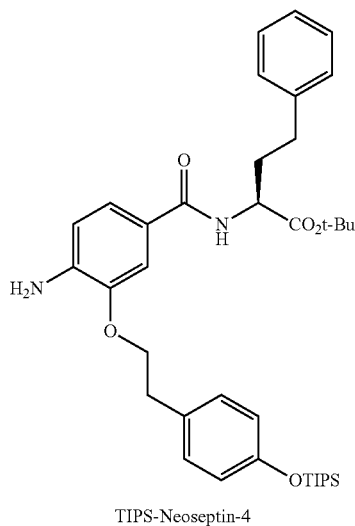

TIPS-Neoseptin-4

0.309 mmol, 1.0 equiv) were dissolved in anhydrous DMF (1.5 mL). 2,6-Lutidine (0.144 mL, 1.24 mmol, 4.0 equiv) was added. Upon dissolution of the reagents, EDCI.HCl (62 mg, 0.325 mmol, 1.05 equiv) was added, and the mixture was stirred 48 hours. After dilution with EtOAc (10 mL), the mixture was washed with 1 N HCl (5 mL), saturated NaHCO$_3$ (5 mL) and brine (5 mL). The organic phase was dried over Na$_2$SO$_4$, decanted and concentrated. The resulting residue was redissolved in anhydrous THF (2 mL) and tetra-n-butylammonium fluoride (TBAF) (1.0 mL, 3.0 equiv, 1 M in THF) was added drop-wise at room temperature. After 30 minutes, H$_2$O (10 mL) was added, and the mixture was diluted with EtOAc (10 mL). The aqueous phase was extracted once with EtOAc (10 mL), and the combined organic phases were dried over Na$_2$SO$_4$, decanted and concentrated. Flash chromatography (40% EtOAc/hexanes) gave 192 mg (89%) of the amide MM-1-315. $^1$H NMR (600 MHz, DMSO-d$_6$) δ 8.45 (d, J=8.4 Hz, 1H), 7.50 (s, 1H), 7.40-7.20 (m, 11H), 7.10 (d, J=7.2 Hz, 2H), 6.65 (d, J=7.1

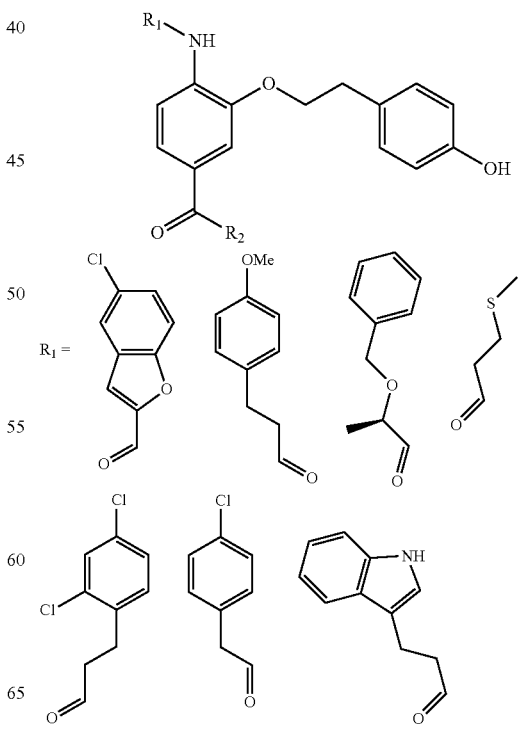

MS-ESI (m/z) calcd for [C$_{31}$H$_{24}$ClFN$_2$O$_5$+H]$^+$ 575.10; found: 575.1; sample wt (mg): 2.7

MS-ESI (m/z) calcd for [C$_{32}$H$_{31}$ClN$_2$O$_5$+H]$^+$ 559.2; found: 559.2; sample wt (mg): 2.85

MS-ESI (m/z) calcd for [C$_{32}$H$_{31}$ClN$_2$O$_5$+H]$^+$ 559.2; found: 559.2; sample wt (mg): 3.14

MS-ESI (m/z) calcd for [C$_{26}$H$_{27}$ClN$_2$O$_4$S+H]$^+$ 499.1; found: 499.1; sample wt (mg): 2.19

MS-ESI (m/z) calcd for [C$_{31}$H$_{27}$Cl$_3$N$_2$O$_4$+H]$^+$ 597.1; found: 597.1; sample wt (mg): 1.76

MS-ESI (m/z) calcd for [C$_{30}$H$_{26}$Cl$_2$N$_2$O$_4$+H]$^+$ 549.1; found: 549.1; sample wt (mg): 1.66

MS-ESI (m/z) calcd for [C$_{33}$H$_{30}$ClN$_3$O$_4$+H]$^+$ 568.2; found: 568.2; sample wt (mg): 1.96

MS-ESI (m/z) calcd for [C$_{27}$H$_{29}$ClN$_2$O$_4$+H]$^+$ 481.2; found: 481.2; sample wt (mg): 2.77

MS-ESI (m/z) calcd for [C$_{34}$H$_{35}$ClN$_2$O$_7$+H]$^+$ 619.2; found: 619.2; sample wt (mg): 2.34

MS-ESI (m/z) calcd for [C$_{32}$H$_{31}$ClN$_2$O$_4$+H]$^+$ 543.2; found: 543.2; sample wt (mg): 3.12

MS-ESI (m/z) calcd for [C$_{31}$H$_{28}$ClFN$_2$O$_4$+H]$^+$ 547.2; found: 547.2; sample wt (mg): 3.72

MS-ESI (m/z) calcd for [C$_{31}$H$_{28}$ClFN$_2$O$_4$+H]$^+$ 597.2; found: 597.2; sample wt (mg): 2.58

MS-ESI (m/z) calcd for [C$_{31}$H24ClFN$_2$O+H]$^+$ 559.13; found: 559.2; sample wt (mg): 1.8

MS-ESI (m/z) calcd for [C$_{32}$H$_{31}$FN$_2$O$_5$+H]$^+$ 543.3; found: 543.3; sample wt (mg): 1.79

MS-ESI (m/z) calcd for [C$_{32}$H$_{31}$FN$_2$O$_5$+H]+543.3; found: 543.3; sample wt (mg): 2.80

MS-ESI (m/z) calcd for [C$_{26}$H$_{27}$FN$_2$O$_4$S+H]$^+$ 483.1; found: 483.1; sample wt (mg): 3.70

MS-ESI (m/z) calcd for [C$_{31}$H$_{27}$Cl$_2$FN$_2$O$_4$+H]$^+$ 581.2; found: 581.2; sample wt (mg): 2.18

MS-ESI (m/z) calcd for [C$_{30}$H$_{26}$ClFN$_2$O$_4$+H]$^+$ 533.2; found: 533.2; sample wt (mg): 1.79

MS-ESI (m/z) calcd for [C$_{33}$H$_{30}$FN$_3$O$_4$+H]$^+$ 552.2; found: 552.2; sample wt (mg): 1.89

MS-ESI (m/z) calcd for [C$_{27}$H$_{29}$FN$_2$O$_4$+H]$^+$ 465.2; found: 465.2; sample wt (mg): 2.13

MS-ESI (m/z) calcd for [C$_{34}$H$_{35}$FN$_2$O$_7$+H]$^+$ 603.2; found: 603.2; sample wt (mg): 3.21

MS-ESI (m/z) calcd for [C$_{32}$H$_{31}$FN$_2$O$_4$+H]$^+$ 527.2; found: 527.2; sample wt (mg): 3.34

MS-ESI (m/z) calcd for [C$_{31}$H$_{28}$F$_2$N$_2$O$_4$+H]$^+$ 531.2; found: 531.2; sample wt (mg): 4.25

MS-ESI (m/z) calcd for [C$_{32}$H$_{28}$F$_4$N$_2$O$_4$+H]$^+$ 581.2; found: 581.2; sample wt (mg): 1.64

55

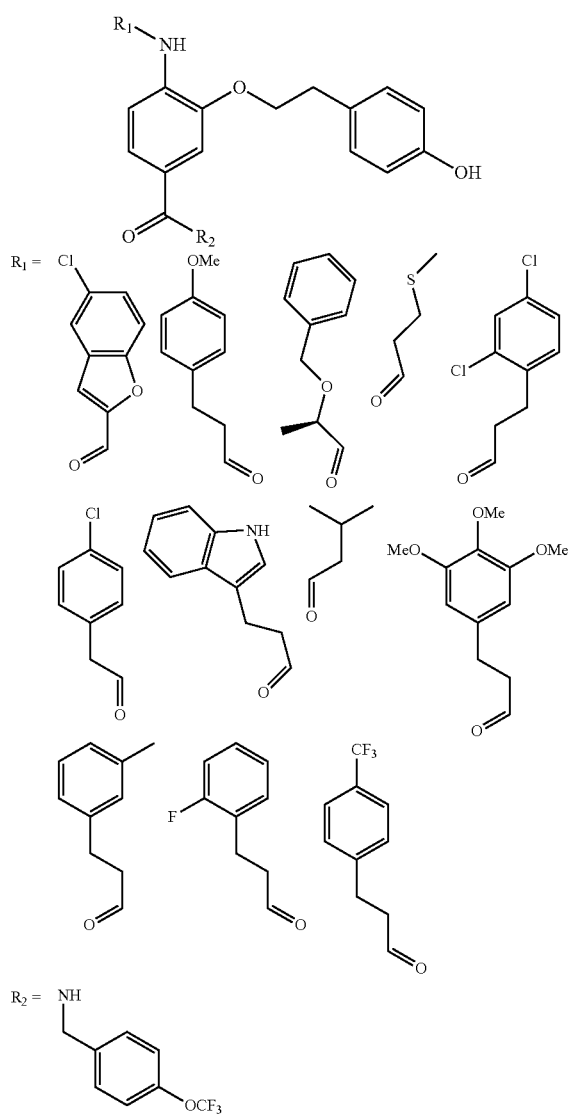

MS-ESI (m/z) calcd for $[C_{31}H_{22}ClF_3N_2O_6+H]^+$; 611.2; found: 611.2; sample wt (mg):3.72

MS-ESI (m/z) calcd for $[C_{32}H_{29}F_3N_2O_6+H]^+$ 595.2; found: 595.2; sample wt (mg): 3.14

MS-ESI (m/z) calcd for $[C_{32}H_{29}F_3N_2O_6+H]^+$ 595.2; found: 595.2; sample wt (mg): 1.14

MS-ESI (m/z) calcd for $[C_{26}H_{25}F3N_2O_5S+H]^+$ 535.1; found: 534.1; sample wt (mg): 2.79

MS-ESI (m/z) calcd for $[C_{31}H_{25}Cl_2F_3N_2O_5+H]^+$; 633.1; found: 633.1; sample wt (mg): 1.83

MS-ESI (m/z) calcd for $[C_{30}H_{24}ClF_3N_2O_5+H]^+$ 585.1; found: 585.2; sample wt (mg): 1.54

MS-ESI (m/z) calcd for $[C_{33}H_{28}F_3N_3O_5+H]^+$ 604.2; found: 604.2; sample wt (mg): 3.89

MS-ESI (m/z) calcd for $[C_{27}H_{27}F_3N_2O+H]^+$ 517.2; found: 517.2; sample wt (mg): 1.87

MS-ESI (m/z) calcd for $[C_{34}H_{33}F3N_2O_8+H]^+$ 655.2; found: 655.2; sample wt (mg): 2.11

MS-ESI (m/z) calcd for $[C_{32}H_{29}F_3N_2O+H]^+$ 579.2; found: 579.2; sample wt (mg): 2.93

MS-ESI (m/z) calcd for $[C_{31}H_{26}F_4N_2O_5+H]^+$ 583.1; found: 583.2; sample wt (mg): 0.86

56

MS-ESI (m/z) calcd for $[C_{32}H_{26}F_6N_2O_5+H]^+$ 633.2; found: 633.2; sample wt (mg): 3.92

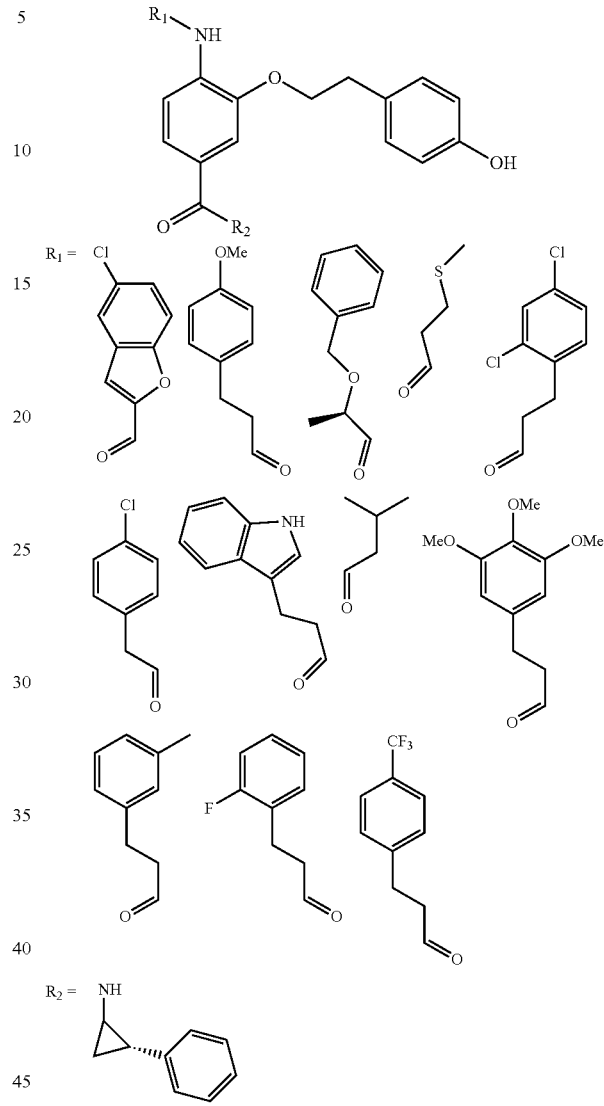

MS-ESI (m/z) calcd for $[C_{33}H_{27}ClN_2O_5+H]^+$ 567.16; found: 567.2; sample wt (mg):2.82

MS-ESI (m/z) calcd for $[C_{34}H_{34}N_2O_5+H]^+$; 551.2; found: 551.2; sample wt (mg): 2.24

MS-ESI (m/z) calcd for $[C_{34}H_{34}N_2O_5+H]^+$; 551.2; found: 551.2; sample wt (mg): 2.24

MS-ESI (m/z) calcd for $[C_{28}H_{30}N_2O_4S+H]^+$ 491.2; found: 491.2 sample wt (mg): 1.80

MS-ESI (m/z) calcd for $[C_{33}H_{30}Cl_2N_2O_4+H]^+$ 589.15; found: 589.2; sample wt (mg): 1.79

MS-ESI (m/z) calcd for $[C_{32}H_{29}ClN_2O_4+H]^+$; 541.1; found: 541.2; sample wt (mg): 1.78

MS-ESI (m/z) calcd for $[C_{35}H_{33}N_3O_4+H]^+$ 560.2; found: 560.2; sample wt (mg): 2.66

MS-ESI (m/z) calcd for $[C_{27}H_{27}F_3N_2O_5+H]^+$ 473.2; found: 473.2; sample wt (mg): 1.45

MS-ESI (m/z) calcd for $[C_{36}H_{36}N_2O_7+H]^+$ 611.2; found: 611.2; sample wt (mg): 2.16

MS-ESI (m/z) calcd for $[C_{34}H_{34}N_2O_4+H]^+$ 535.2; found: 535.2; sample wt (mg): 1.39

MS-ESI (m/z) calcd for $[C_{33}H_{31}FN_2O_4+H]^+$ 538.2; found: 538.2; sample wt (mg): 3.92

MS-ESI (m/z) calcd for $[C_{34}H_{31}F_3N_2O_4+H]^+$ 589.2; found: 589.2; sample wt (mg): 6.12

MS-ESI (m/z) calcd for $[C_{32}H_{30}ClFN_2O_4+H]^+$; 561.2; found: 561.2; sample wt (mg): 2.6

MS-ESI (m/z) calcd for $[C_{33}H_{30}ClF_3N_2O_4+H]^+$; 611.2; found: 611.2; sample wt (mg): 5.37

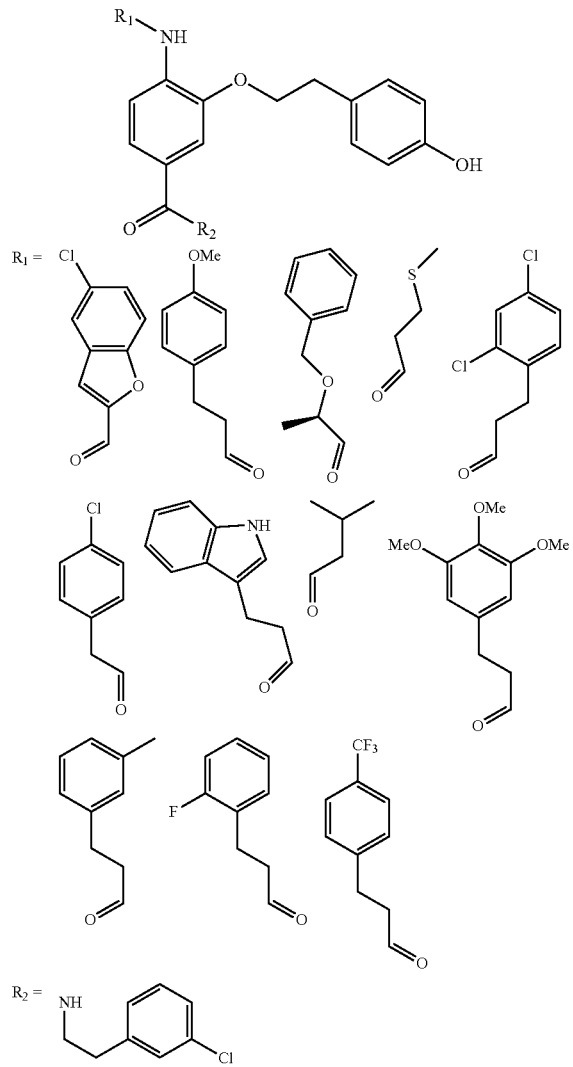

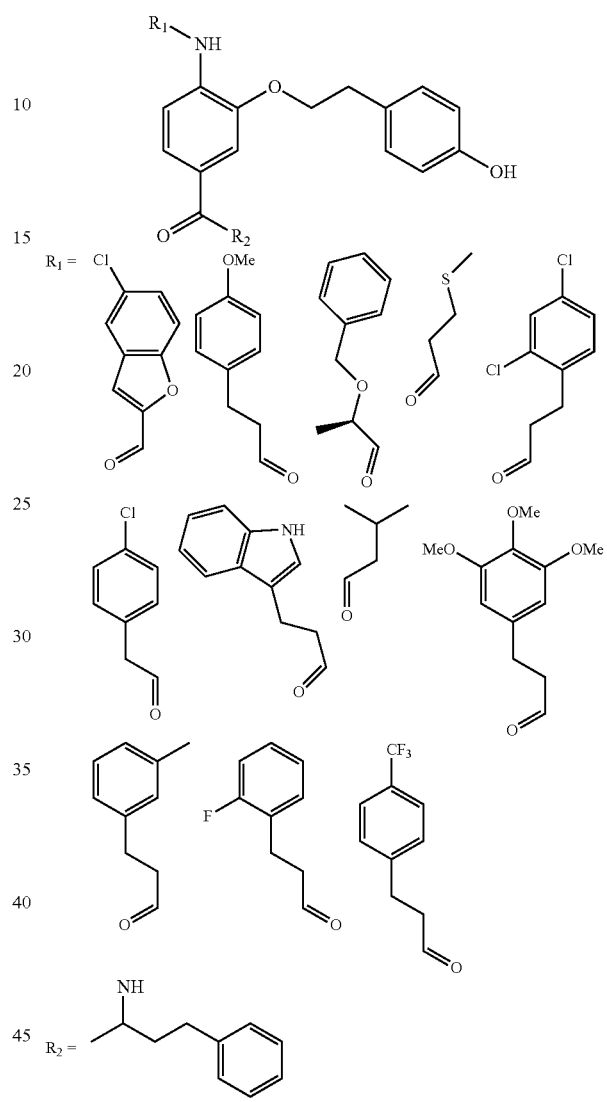

MS-ESI (m/z) calcd for $[C_{32}H_{26}Cl_2N_2O_5+H]^+$ 589.2; found: 589.2; sample wt (mg):3.14

MS-ESI (m/z) calcd for $[C_{33}H_{33}ClN_2O_5+H]^+$ 573.2; found: 573.2; sample wt (mg): 2.12

MS-ESI (m/z) calcd for $[C_{33}H_{33}ClN_2O_5+H]^+$ 573.2; found: 573.2; sample wt (mg): 2.23

MS-ESI (m/z) calcd for $[C_{27}H_{29}ClN_2O_4S+H]^+$ 513.1; found: 513.1; sample wt (mg): 1.69

MS-ESI (m/z) calcd for $[C_{32}H29Cl_3N_2O_4+H]^+$ 611.1; found: 611.2; sample wt (mg): 1.67

MS-ESI (m/z) calcd for $[C_{31}H_{28}Cl_2N_2O_4+H]^+$ 563.1; found: 563.2; sample wt (mg): 2.84

MS-ESI (m/z) calcd for $[C_{34}H_{32}ClN_3O_4+H]^+$ 582.2; found: 582.2; sample wt (mg): 2.14

MS-ESI (m/z) calcd for $[C_{28}H_{31}ClN_2O_4+H]^+$ 495.2; found: 495.2; sample wt (mg): 1.69

MS-ESI (m/z) calcd for $[C_{35}H_{37}ClN_2O_7+H]^+$ 633.2; found: 633.2; sample wt (mg): 2.12

MS-ESI (m/z) calcd for $[C_{33}H_{33}ClN_2O_4+H]^+$ 557.2; found: 557.2; sample wt (mg): 2.18

MS-ESI (m/z) calcd for $[C_{34}H_{31}ClN_2O_5+H]^+$ 583.2; found: 583.2; sample wt (mg):1.69

MS-ESI (m/z) calcd for $[C_{35}H_{38}N_2O_5]^+$ 567.2; found: 567.2; sample wt (mg): 1.92

MS-ESI (m/z) calcd for $[C_{35}H_{38}N_2O_5]^+$ 567.2; found: 567.2; sample wt (mg): 1.79

MS-ESI (m/z) calcd for $[C_{29}H_{34}N_2O_4S+H]^+$ 507.2; found: 507.2 sample wt (mg): 1.19

MS-ESI (m/z) calcd for $[C_{32}H_{29}Cl_3N_2O_4+H]^+$ 605.2; found: 605.2; sample wt (mg): 1.39

MS-ESI (m/z) calcd for $[C_{33}H_{33}ClN_2O_4+H]^-$ 557.2; found: 557.2; sample wt (mg): 2.53

MS-ESI (m/z) calcd for $[C_{36}H_{37}N_3O_4+H]^+$ 576.2; found: 576.2; sample wt (mg): 1.74

MS-ESI (m/z) calcd for $[C_{30}H_{36}N_2O_4+H]^+$ 489.2; 989.2; sample wt (mg): 2.12

MS-ESI (m/z) calcd for $[C_{37}H_{42}N_2O_7+H]^+$ 627.2; found: 627.2; sample wt (mg): 2.26

59

MS-ESI (m/z) calcd for $[C_{35}H_{38}N_2O_4+H]^+$ 551.2; found: 551.2; sample wt (mg): 2.72

MS-ESI (m/z) calcd for $[C_{34}H_{35}FN_2O_4+H]^+$ 555.2; found: 555.2; sample wt (mg): 2.87

MS-ESI (m/z) calcd for $[C_{35}H_{35}F_3N_2O_4+H]^+$ 605.2; found: 605.2; sample wt (mg): 9.71

60

MS-ESI (m/z) calcd for $[C_{34}H_{33}F_3N_2O_8+H]^+$ 655.2; found: 655.2; sample wt (mg): 2.21

MS-ESI (m/z) calcd for $[C_{32}H_{29}F_3N_2O+H]^+$ 579.2; found: 579.2; sample wt (mg): 2.16

MS-ESI (m/z) calcd for $[C_{31}H_{26}F_4N_2O_5+H]^+$ 583.1; found: 583.2; sample wt (mg): 3.13

MS-ESI (m/z) calcd for $[C_{32}H_{26}F_6N_2O_5+H]^+$ 633.2; found: 633.2; sample wt (mg): 3.92

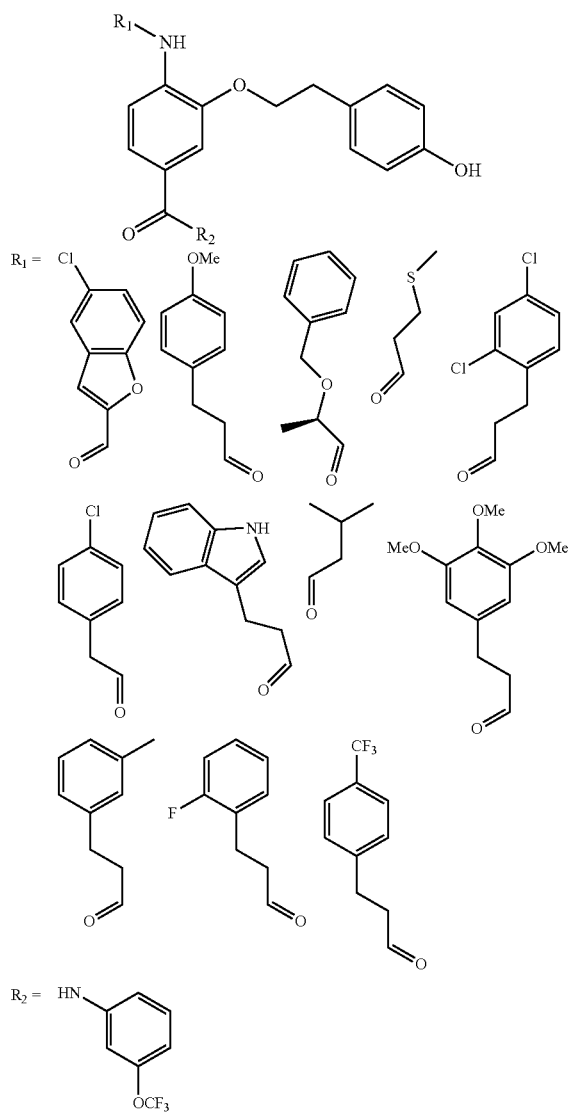

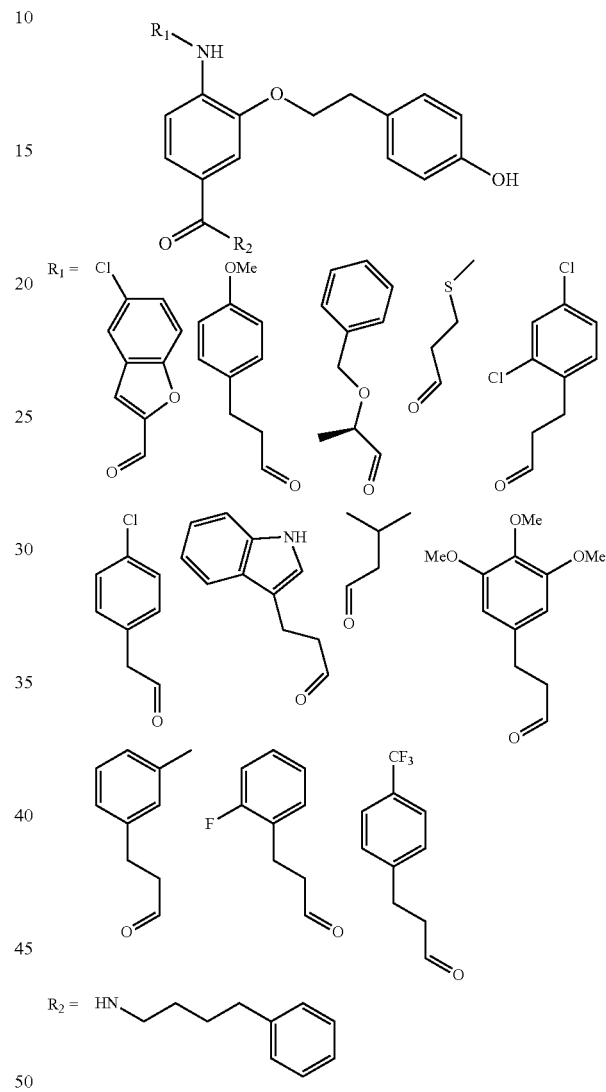

MS-ESI (m/z) calcd for $[C_{31}H_{22}ClF_3N_2O_6+H]^+$; 611.2; found: 611.2; sample wt (mg):1.69

MS-ESI (m/z) calcd for $[C_{32}H_{29}F_3N_2O_6+H]^+$ 595.2; found: 595.2; sample wt (mg): 2.14

MS-ESI (m/z) calcd for $[C_{32}H_{29}F_3N_2O_6+H]^+$ 595.2; found: 595.2; sample wt (mg): 3.11

MS-ESI (m/z) calcd for $[C_{26}H_{25}F3N_2O_5S+H]^+$ 535.1; found: 534.1; sample wt (mg): 2.12

MS-ESI (m/z) calcd for $[C_{31}H_{25}Cl_2F_3N_2O_5+H]^+$; 633.1; found: 633.1; sample wt (mg): 2.09

MS-ESI (m/z) calcd for $[C_{30}H_{24}ClF_3N_2O_5+H]^+$ 585.1; found: 585.2; sample wt (mg): 1.89

MS-ESI (m/z) calcd for $[C_{33}H_{28}F_3N_3O_5+H]^+$ 604.2; found: 604.2; sample wt (mg): 2.84

MS-ESI (m/z) calcd for $[C_{27}H_{27}F_3N_2O+H]^+$ 517.2; found: 517.2; sample wt (mg): 2.34

MS-ESI (m/z) calcd for $[C_{34}H_{31}ClN_2O_5+H]^+$ 583.2; found: 583.2; sample wt (mg):4.06

MS-ESI (m/z) calcd for $[C_{35}H_{38}N_2O_5+H]^+$ 567.2; found: 567.2 sample wt (mg): 3.09

MS-ESI (m/z) calcd for $[C_{35}H_{38}N_2O_5+H]^+$ 567.2; found: 567.2 sample wt (mg): 299

MS-ESI (m/z) calcd for $[C_{29}H_{34}N_2O_4S+H]^+$ 507.2; found: 507.2 sample wt (mg): 1.29

MS-ESI (m/z) calcd for $[C_{34}H_{34}Cl_2N_2O_4+H]^+$ 605.2; found: 605.2 sample wt (mg): 2.23

MS-ESI (m/z) calcd for $[C_{33}H_{33}ClN_2O_4+H]^+$ 557.2; found: 557.2 sample wt (mg): 2.68

MS-ESI (m/z) calcd for $[C_{36}H_{37}N_3O_4+H]^+$ 576.2; found: 576.2 sample wt (mg): 1.98

MS-ESI (m/z) calcd for $[C_{30}H_{36}N_2O_4+H]^+$ 489.2; found: 489.2 sample wt (mg): 2.14

MS-ESI (m/z) calcd for $[C_{37}H_{42}N_2O_7+H]^+$ 627.2; found: 627.2; sample wt (mg): 2.17
MS-ESI (m/z) calcd for $[C_{35}H_{38}N_2O_4+H]^+$ 551.2; found: 551.2; sample wt (mg): 3.13
MS-ESI (m/z) calcd for $[C_{34}H_{35}FN_2O_4+H]^+$ 555.2; found: 555.2; sample wt (mg): 1.89
MS-ESI (m/z) calcd for $[C_{35}H_{35}F_3N_2O_4+H]^+$ 605.2; found: 605.2; sample wt (mg): 2.89

MS-ESI (m/z) calcd for $[C_{27}H_{29}ClN_2O_4+H]^+$ 481.2; found: 481.2; sample wt (mg): 2.83
MS-ESI (m/z) calcd for $[C_{34}H_{35}ClN_2O_7+H]^+$ 619.2; found: 619.2; sample wt (mg): 2.18
MS-ESI (m/z) calcd for $[C_{32}H_{31}ClN_2O_4+H]^+$ 543.2; found: 543.2; sample wt (mg): 3.34
MS-ESI (m/z) calcd for $[C_{31}H_{28}ClFN_2O_4+H]^+$ 547.2; found: 547.2; sample wt (mg): 2.44
MS-ESI (m/z) calcd for $[C_{31}H_{28}ClFN_2O_4+H]^+$ 597.2; found: 597.2; sample wt (mg): 5.26

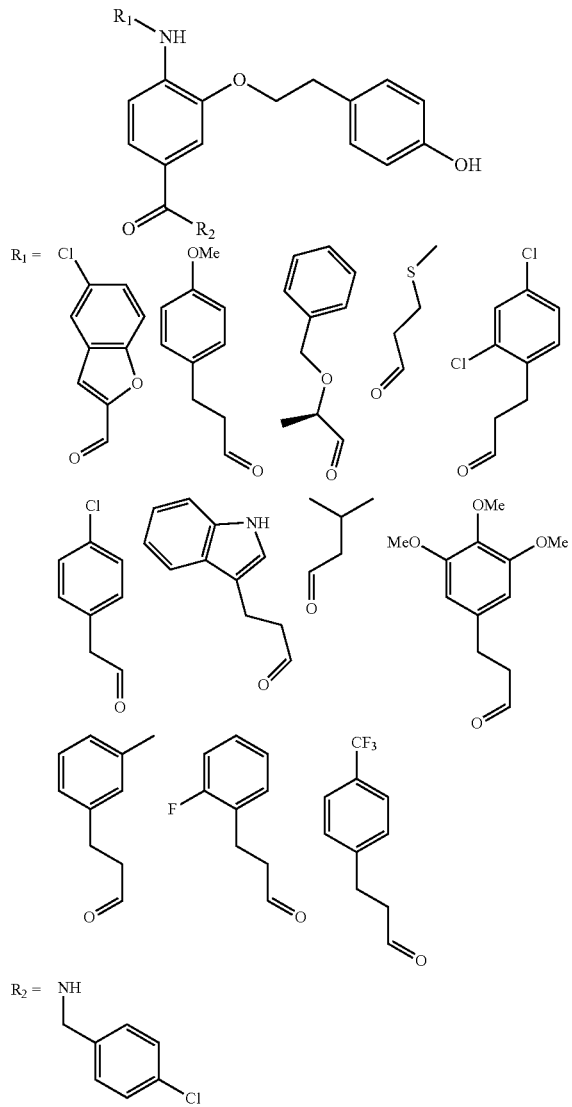

MS-ESI (m/z) calcd for $[C_{31}H_{24}ClFN_2O_5+H]^+$ 575.10; found: 575.1; sample wt (mg): 1.76
MS-ESI (m/z) calcd for $[C_{32}H_{31}ClN_2O_5+H]^+$ 559.2; found: 559.2; sample wt (mg): 3.85
MS-ESI (m/z) calcd for $[C_{32}H_{31}ClN_2O_5+H]^+$ 559.2; found: 559.2; sample wt (mg): 1.89
MS-ESI (m/z) calcd for $[C_{26}H_{27}ClN_2O_4S+H]^+$ 499.1; found: 499.1; sample wt (mg): 1.95
MS-ESI (m/z) calcd for $[C_{31}H_{27}Cl_3N_2O_4+H]^+$ 597.1; found: 597.1; sample wt (mg): 1.88
MS-ESI (m/z) calcd for $[C_{30}H_{26}Cl_2N_2O_4+H]^+$ 549.1; found: 549.1; sample wt (mg): 1.74
MS-ESI (m/z) calcd for $[C_{33}H_{30}ClN_3O_4+H]^+$ 568.2; found: 568.2; sample wt (mg): 2.17

MS-ESI (m/z) calcd for $[C_{31}H_{23}Cl_3N_2O_5+H]^+$ 609.2; found: 609.2; sample wt (mg): 3.91
MS-ESI (m/z) calcd for $[C_{32}H_{30}Cl_2N_2O_5+H]^+$ 593.1; found: 593.1; sample wt (mg): 2.58
MS-ESI (m/z) calcd for $[C_{32}H_{30}Cl_2N_2O_5+H]^+$ 593.2; found: 593.2; sample wt (mg): 1.68
MS-ESI (m/z) calcd for $[C_{26}H_{26}Cl_2N_2O_4S+H]^+$ 533.2; found: 533.2; sample wt (mg): 2.18
MS-ESI (m/z) calcd for $([C_{31}H_{26}Cl_4N_2O_4+H]^+$ 631.2; found: 631.2; sample wt (mg): 1.67
MS-ESI (m/z) calcd for $[C_{30}H_{25}Cl_3N_2O_4+H]^+$ 583.1; found: 583.1; sample wt (mg): 3.13

MS-ESI (m/z) calcd for $[C_{33}H_{29}Cl_2N_3O_4+H]^+$ 602.2; found: 602.2; sample wt (mg): 1.78
MS-ESI (m/z) calcd for $[C_{27}H_{28}Cl_2N_2O_4+H]^+$ 515.2; found: 515.2; sample wt (mg): 2.09
MS-ESI (m/z) calcd for $[C_{34}H_{34}Cl_2N_2O_7+H]^+$ 653.2; found: 653.2; sample wt (mg): 3.13
MS-ESI (m/z) calcd for $[C_{32}H_{30}Cl_2N_2O_4+H]^+$ 577.2; found: 577.2; sample wt (mg): 3.12
MS-ESI (m/z) calcd for $[C_{31}H_{27}Cl_2FN_2O_4+H]^+$ 581.2; found: 581.2; sample wt (mg): 5.26
MS-ESI (m/z) calcd for $[C_{32}H_{27}Cl_2F_3N_2O_4+H]^+$ 631.2; found: 631.2; sample wt (mg): 5.1

MS-ESI (m/z) calcd for $[C_{30}H_{26}ClFN_2O_4+H]^+$ 533.2; found: 533.2; sample wt (mg): 1.54
MS-ESI (m/z) calcd for $[C_{33}H_{30}FN_3O_4+H]^+$ 552.2; found: 552.2; sample wt (mg): 1.79
MS-ESI (m/z) calcd for $[C_{27}H_{29}FN_2O_4+H]^+$ 465.2; found: 465.2; sample wt (mg): 2.13
MS-ESI (m/z) calcd for $[C_{34}H_{35}FN_2O_7+H]^+$ 603.2; found: 603.2; sample wt (mg): 3.07
MS-ESI (m/z) calcd for $[C_{32}H_{31}FN_2O_4+H]^+$ 527.2; found: 527.2; sample wt (mg): 3.15
MS-ESI (m/z) calcd for $[C_{31}H_{28}F_2N_2O_4+H]^+$ 531.2; found: 531.2; sample wt (mg): 2.15
MS-ESI (m/z) calcd for $[C_{32}H_{28}F_4N_2O_4+H]^+$ 581.2; found: 581.2; sample wt (mg): 1.68

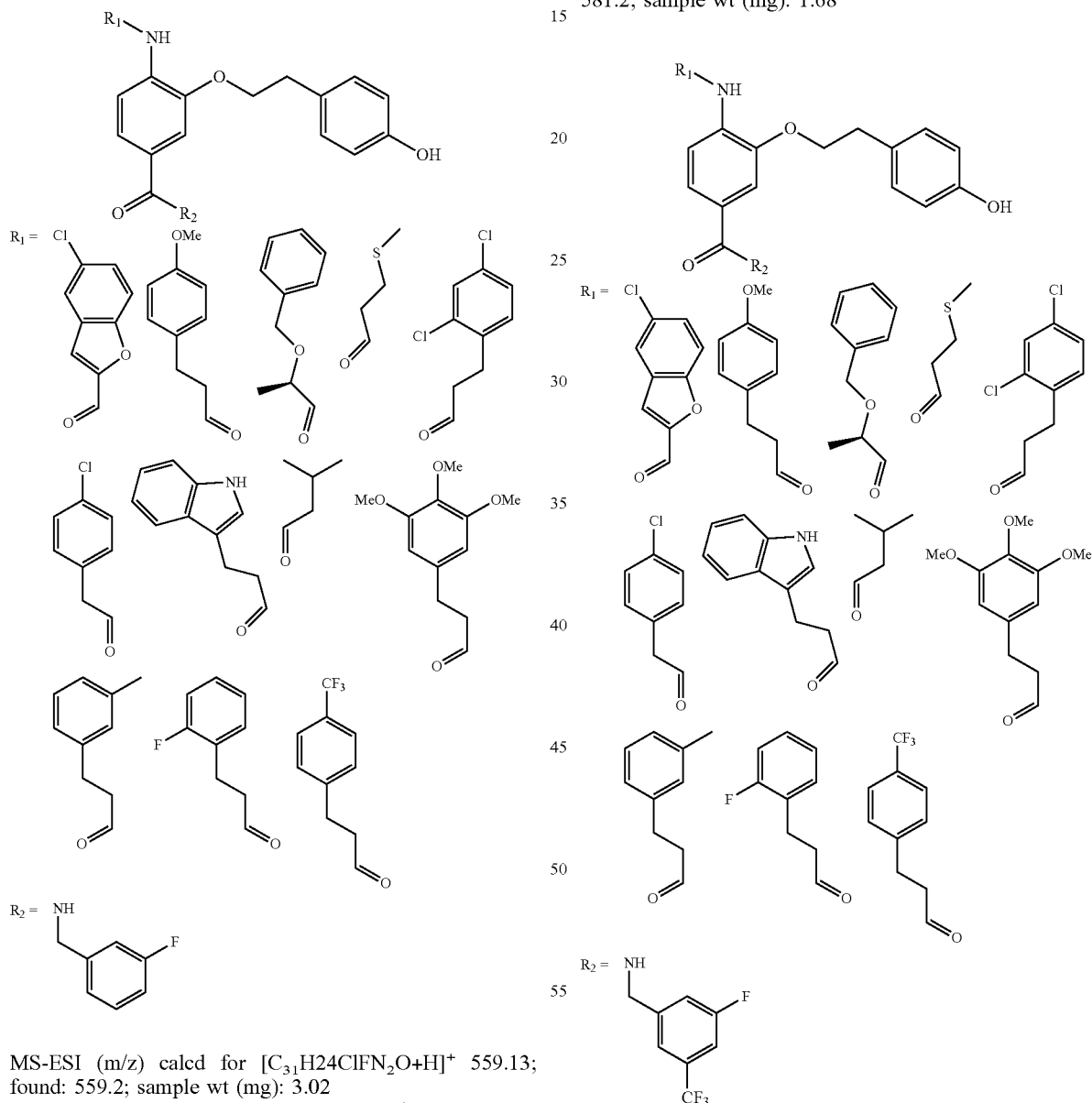

MS-ESI (m/z) calcd for $[C_{31}H24ClFN_2O+H]^+$ 559.13; found: 559.2; sample wt (mg): 3.02
MS-ESI (m/z) calcd for $[C_{32}H_{31}FN_2O_5+H]^+$ 543.3; found: 543.3; sample wt (mg): 1.79
MS-ESI (m/z) calcd for $[C_{32}H_{31}FN_2O_5+H]$+543.3; found: 543.3; sample wt (mg): 3.09
MS-ESI (m/z) calcd for $[C_{26}H_{27}FN_2O_4S+H]^+$ 483.1; found: 483.1; sample wt (mg): 2.35
MS-ESI (m/z) calcd for $[C_{31}H_{27}Cl_2FN_2O_4+H]^+$ 581.2; found: 581.2; sample wt (mg): 3.31

MS-ESI (m/z) calcd for $[C_{32}H_{23}ClF_4N_2O_5+H]^+$ 627.1; found: 627.1; sample wt (mg):2.53
MS-ESI (m/z) calcd for $[C_{33}H_{30}F_4N_2O_5+H]^+$ 611.2; found: 611.2; sample wt (mg): 3.19
MS-ESI (m/z) calcd for $[C_{33}H_{30}F_4N_2O_5+H]^+$ 611.2; found: 611.2; sample wt (mg): 2.29

MS-ESI (m/z) calcd for $[C_{27}H_{26}F_4N_2O_4S+H]^+$; 551.1; found: 551.16; sample wt (mg): 2.29
MS-ESI (m/z) calcd for $[C_{32}H_{26}Cl2F_4N_2O_4+H]^+$ 649.1; found: 649.2; sample wt (mg): 2.18
MS-ESI (m/z) calcd for $[C_{31}H_{25}ClF_4N_2O_4+H]^+$ 601.1. found: 601.2; sample wt (mg): 1.88
MS-ESI (m/z) calcd for $[C_{34}H_{29}F_4N_3O_4+H]^+$ 620.2; found: 620.2; sample wt (mg): 1.43
MS-ESI (m/z) calcd for $[C_{28}H_{28}F_4N_2O_4+H]^+$ 533.2; found: 533.2; sample wt (mg): 2.81
MS-ESI (m/z) calcd for $[C_{35}H_{34}F_4N_2O_7+H]^+$ 671.2; found: 671.2; sample wt (mg): 3.18
MS-ESI (m/z) calcd for $[C_{33}H_{30}F_4N_2O_4+H]^+$ 595.2; found: 595.2; sample wt (mg): 2.76
MS-ESI (m/z) calcd for $[C_{32}H_{27}F_5N_2O_4+H]^+$ 599.2; found: 599.2; sample wt (mg): 2.43
MS-ESI (m/z) calcd for $[C_{33}H_{27}F_7N_2O_4+H]^+$ 649.2; found: 649.2; sample wt (mg): 6.12

MS-ESI (m/z) calcd for $[C_{28}H_{31}FN_2O_4S+H]^+$ 511.2. found: 511.2; sample wt (mg):1.69
MS-ESI (m/z) calcd for $[C_{33}H_{31}Cl_2FN_2O_4+H]^+$; 609.2; found: 609.2; sample wt (mg): 3.08
MS-ESI (m/z) calcd for $[C_{32}H_{30}ClFN_2O_4+H]^+$ 561.1; found: 561.1; sample wt (mg): 1.78
MS-ESI (m/z) calcd for $[C_{35}H_{34}FN_3O_4+H]^+$ 580.2; found: 580.2 sample wt (mg): 2.84
MS-ESI (m/z) calcd for $[C_{29}H_{33}FN_2O_4+H]^+$ 493.2; found: 493.2; sample wt (mg): 1.98
MS-ESI (m/z) calcd for $[C_{36}H_{39}FN_2O_7+H]^+$ 631.2; found: 631.2; sample wt (mg): 2.26
MS-ESI (m/z) calcd for $[C_{34}H_{35}FN_2O_4+H]^+$ 555.2; found: 555.2; sample wt (mg): 2.97
MS-ESI (m/z) calcd for $[C_{33}H_{32}F_2N_2O_4+H]^+$ 559.2; found: 559.2; sample wt (mg): 5.6
MS-ESI (m/z) calcd for $[C_{34}H_{32}F_4N_2O_4+H]^+$ 609.2; found: 609.2; sample wt (mg): 0.98

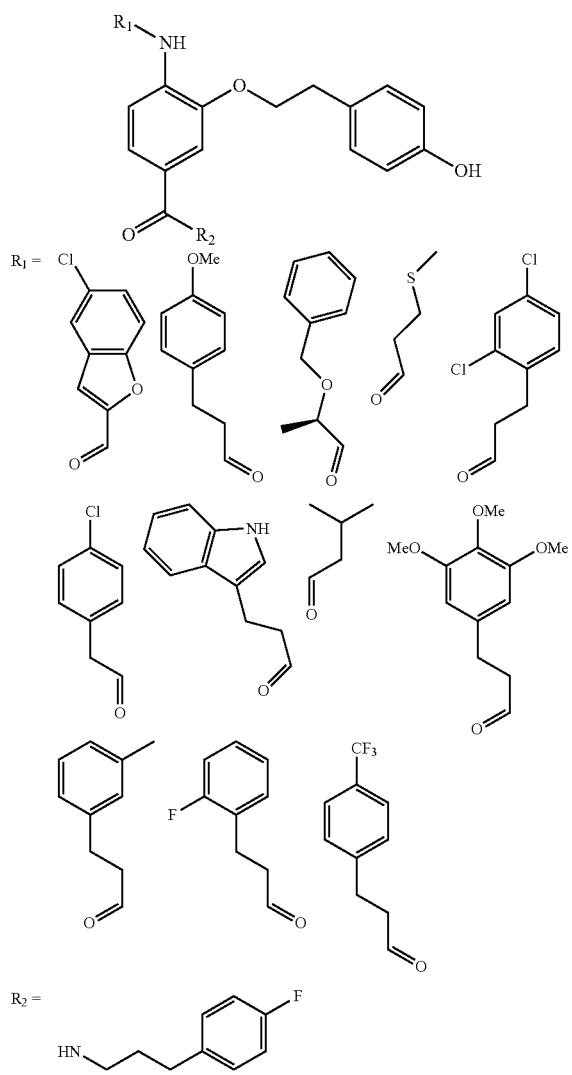

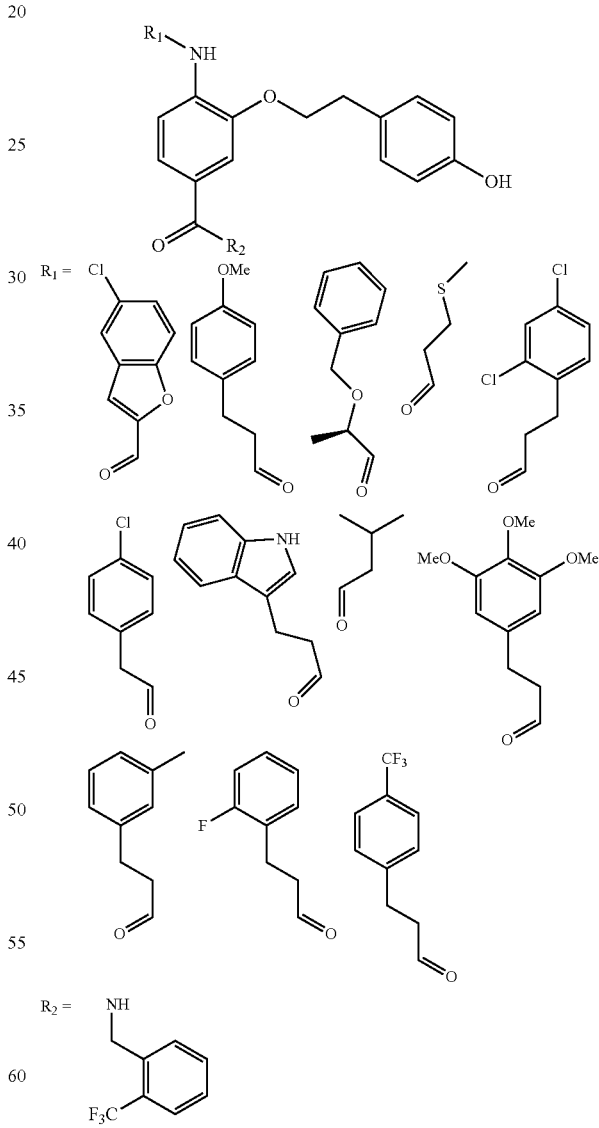

MS-ESI (m/z) calcd for $[C_{33}H_{28}ClFN_2O_5+H]^+$ 587.2. found: 587.2; sample wt (mg):2.79
MS-ESI (m/z) calcd for $[C_{34}H_{35}FN_2O_5+H]^+$ 571.2; found: 571.2; sample wt (mg): 2.18
MS-ESI (m/z) calcd for $[C_{34}H_{35}FN_2O_5+H]^+$ 571.2; found: 571.2; sample wt (mg): 3.12

MS-ESI (m/z) calcd for $[C_{32}H_{24}ClF_3N_2O_5+H]^+$ 609.1; found: 609.1 sample wt (mg):2.49
MS-ESI (m/z) calcd for $[C_{33}H_{31}F_3N_2O_5+H]^+$ 593.2; found: 593.2; sample wt (mg): 2.35

MS-ESI (m/z) calcd for $[C_{33}H_{31}F_3N_2O_5+H]^+$ 593.2; found: 593.2; sample wt (mg): 2.15
MS-ESI (m/z) calcd for $[C_{27}H_{27}F_3N_2O_4S+H]^+$ 533.1; found: 533.1; sample wt (mg):1.93
MS-ESI (m/z) calcd for $[C_{32}H_{27}Cl_2F_3N_2O_4+H]^+$ 631.2; found: 631.2; sample wt (mg): 3.13
MS-ESI (m/z) calcd for $[C_{31}H_{26}ClF_3N_2O+H]^+$ 583.1; found: 583.1; sample wt (mg): 1.98
MS-ESI (m/z) calcd for $[C_{34}H_{30}F_3N_3O_4+H]^+$ 602.2; found: 602.2; sample wt (mg): 2.62
MS-ESI (m/z) calcd for $[C_{28}H_{29}F_3N_2O_4+H]^+$ 515.2; found: 515.2; sample wt (mg): 2.93
MS-ESI (m/z) calcd for $[C_{34}H_{36}N_2O_7+H]^+$ 585.2. found: 585.2 sample wt (mg): 1.96
MS-ESI (m/z) calcd for $[C_{33}H_{31}F_3N_2O_4+H]^+$ 577.2; found: 577.2; sample wt (mg):2.48
MS-ESI (m/z) calcd for $[C_{32}H_{28}F_4N_2O_4+H]^+$ 581.2; found: 581.2; sample wt (mg): 1.97
MS-ESI (m/z) calcd for $[C33H_{28}F_6N_2O_4+H]^+$ 631.2; found: 631.2; sample wt (mg): 2.64

MS-ESI (m/z) calcd for $[C_{32}H_{32}N_2O_5+H]^+$ 525.2; found: 525.2; sample wt (mg): 1.94
MS-ESI (m/z) calcd for $[C_{32}H_{32}N_2O_5+H]^+$ 525.2; found: 525.2; sample wt (mg): 2.15
MS-ESI (m/z) calcd for $[C_{26}H_{28}N_2O_4S+H]^+$ 464.1. found: 464.1; sample wt (mg):1.83
MS-ESI (m/z) calcd for $[C_{31}H_{28}Cl_2N_2O_4+H]^+$ 563.2; found: 563.2; sample wt (mg): 2.82
MS-ESI (m/z) calcd for $[C_{30}H_{27}ClN_2O_4+H]^+$ 515.1; found: 515.1; sample wt (mg): 2.28
MS-ESI (m/z) calcd for $[C_{33}H_{31}N_3O_4+H]^+$ 534.2; found: 534.2; sample wt (mg): 1.89
MS-ESI (m/z) calcd for $[C_{28}H_{29}F_3N_2O_4+H]^+$ 447.2; found: 447.2; sample wt (mg): 1.73
MS-ESI (m/z) calcd for $[C_{34}H_{36}N_2O_7+H]^+$ 585.2. found: 585.2 sample wt (mg): 1.96
MS-ESI (m/z) calcd for $[C_{32}H_{32}N_2O_4+H]$ 509.2; found: 509.2; sample wt (mg): 2.33
MS-ESI (m/z) calcd for $C_{31}H_{29}FN_2O_4$ [M+H]+; 513.2; found: 513.2; sample wt (mg): 3.35
MS-ESI (m/z) calcd for $[C_{32}H_{29}F_3N_2O_4+H]$ 563.2; found: 563.2; sample wt (mg): 6.12

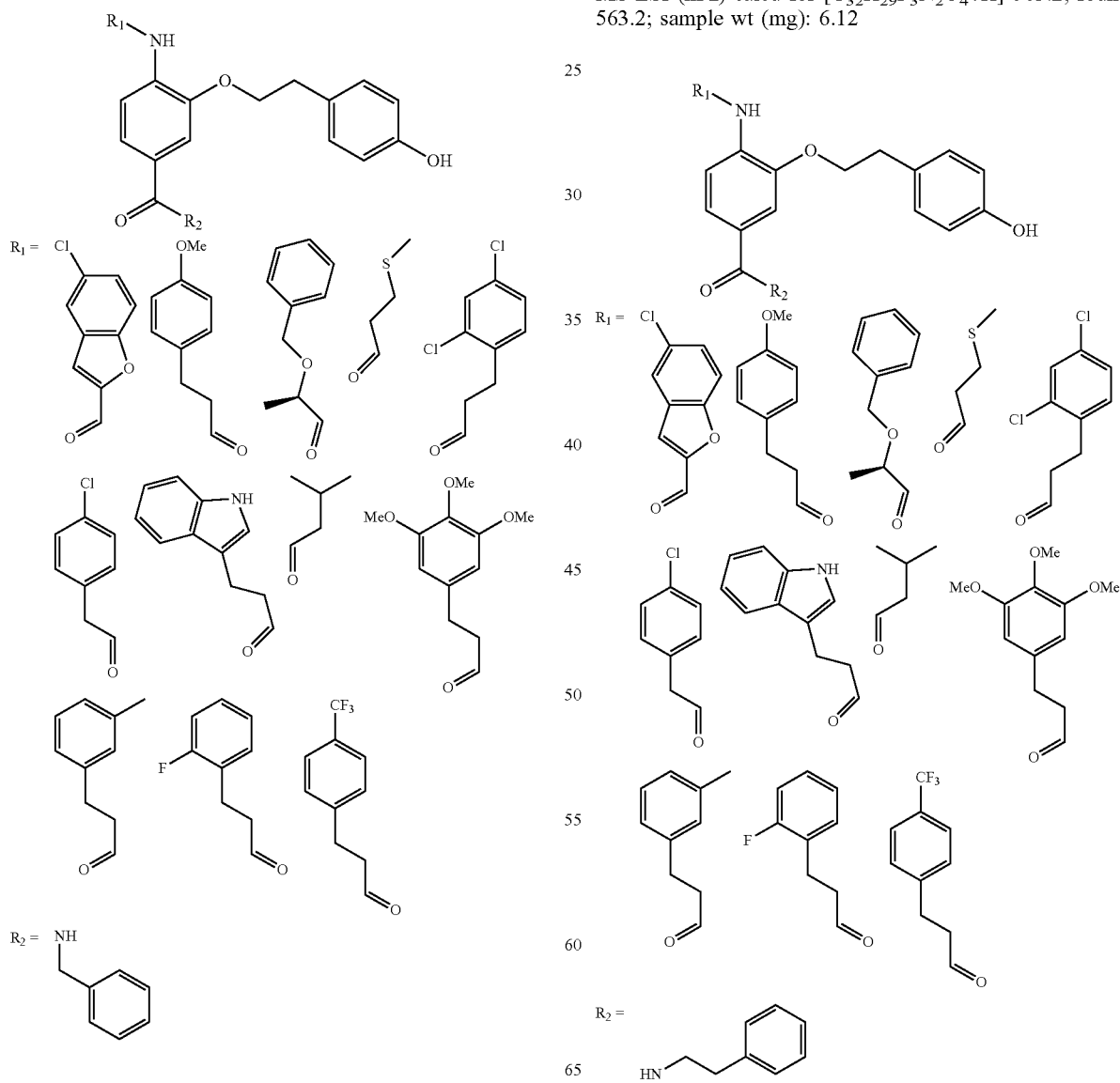

MS-ESI (m/z) calcd for $[C_{31}H_{25}ClN_2O_5+H]^+$ 541.1; found: 541.1; sample wt (mg):4.18

MS-ESI (m/z) calcd for $[C_{32}H_{27}ClN_2O_5+H]^+$ 555.1; found: 555.1; sample wt (mg): 1.2
MS-ESI (m/z) calcd for $[C_{33}H_{34}N_2O_5+H]^+$ 539.9; found: 539.2 sample wt (mg): 1.86
MS-ESI (m/z) calcd for $[C_{33}H_{34}N_2O_5+H]^+$ 539.9; found: 539.2 sample wt (mg): 2.28
MS-ESI (m/z) calcd for $[C_{27}H_{30}N_2O_4S+H]^+$ 479.2; found: 479.2 sample wt (mg):2.21
MS-ESI (m/z) calcd for $[C_{32}H_{30}Cl_2N_2O_4+H]^+$ 577.2; found: 577.2; sample wt (mg): 2.04
MS-ESI (m/z) calcd for $[C_{31}H_{29}ClN_2O_4+H]^+$ 529.2; found: 529.2; sample wt (mg): 1.18
MS-ESI (m/z) calcd for $[C_{34}H_{33}N_3O_4+H]^+$ 548.2; found: 548.2; sample wt (mg): 1.89
MS-ESI (m/z) calcd for $[C_{28}H_{32}N_2O_4+H]^+$ 461.2; found: 461.2; sample wt (mg): 2.04
MS-ESI (m/z) calcd for $[C_{40}H_{40}N_2O_7+H]^+$ 599.2. found: 599.2 sample wt (mg): 1.98
MS-ESI (m/z) calcd for $[C_{33}H_{34}N_2O_4+H]^+$ 523.2; found: 523.2; sample wt (mg):1.83
MS-ESI (m/z) calcd for $[C_{32}H_{31}FN_2O_4+H]^+$ 527.2; found: 527.2; sample wt (mg): 2.98
MS-ESI (m/z) calcd for $[C_{33}H_{31}F_3N_2O_4+H]^+$ 577.2; found: 577.2; sample wt (mg): 2.74

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A compound that corresponds in structure to Formula I, below, or its pharmaceutically acceptable salt

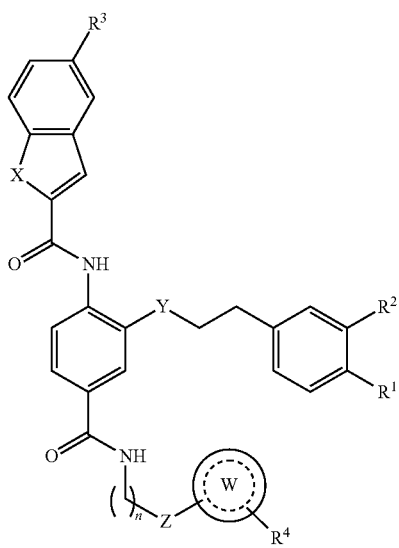

wherein
X is O, S, $NR^5$, or $CH_2$, where $R^5$ is hydrido (H), or $C_1$-$C_4$ hydrocarbyl;
Y is O, $CH_2$, or absent;
Z is O, S, $NR^6$, or $CH_2$, where $R^6$ is hydrido, or $C_1$-$C_4$ hydrocarbyl;
n is a number that is zero, 1 or 2, but n is only zero when Z is $CH_2$;

$R^1$ is H or OH, $R^2$ is H or OH, or $R^1$ is OH and $R^2$ is OH, but at least one of $R^1$ and $R^2$ is OH;

$R^3$ is hydrido, halogen, azido, $C_1$-$C_4$ hydrocarbyl, $C_1$-$C_4$ hydrocarbyloxy or trifluoromethyl;

$R^4$ is hydrido, halogen, azido, $C_1$-$C_4$ hydrocarbyl, $C_1$-$C_4$ hydrocarbyloxy or trifluoromethyl;

W is phenyl ring that contains one to three substituent groups collectively referred to as $R^4$ that include one or more substituents selected from the group consisting of hydrido, hydroxyl, $C_1$-$C_4$ hydrocarbyl, $C_1$-$C_4$ hydrocarbyloxy, halogen, and trifluoromethyl bonded to one or more ring atoms.

2. The compound or its pharmaceutically acceptable salt according to claim 1, wherein X is O or $NR^5$.

3. The compound or its pharmaceutically acceptable salt according to claim 1, wherein Y is O.

4. The compound according to claim 1 that corresponds in structure to Formula II, below, or its pharmaceutically acceptable salt

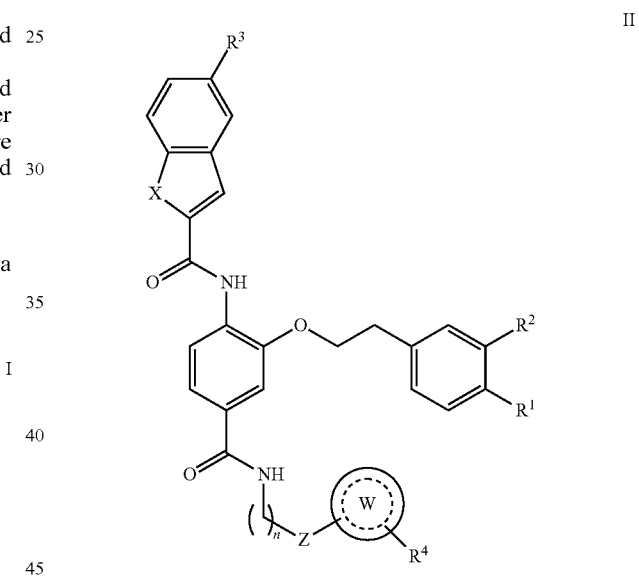

where Z, n, $R^1$, $R^2$, $R^3$, $R^4$ and $R^5$ are as defined above, and X is O or $NR^5$.

5. The compound or its pharmaceutically acceptable salt according to claim 4, wherein X is O.

6. The compound or its pharmaceutically acceptable salt according to claim 4, wherein Z is $CH_2$.

7. The compound or its pharmaceutically acceptable salt according to claim 4, wherein said phenyl ring contains a single substituent $R^4$ that is hydrido or halo.

8. The compound or its pharmaceutically acceptable salt according to claim 5, wherein $R^4$ is a single substituent that is a meta- or para-substituted halogen, azido, $C_1$-$C_4$ hydrocarbyl, $C_1$-$C_4$ hydrocarbyloxy, or a trifluoromethyl group.

9. The compound or its pharmaceutically acceptable salt according to claim 5, wherein $R^2$ is hydrido and $R^1$ is hydroxyl.

10. A compound corresponding in structure to the structural formula below, or a pharmaceutically acceptable salt thereof 71
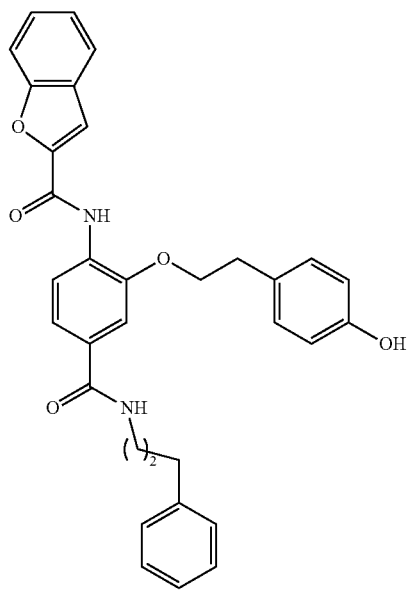
72
-continued
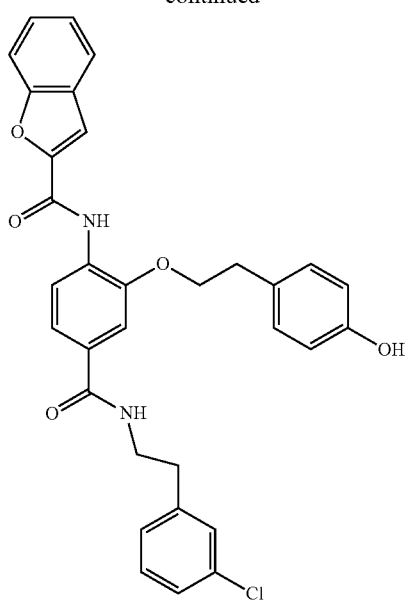
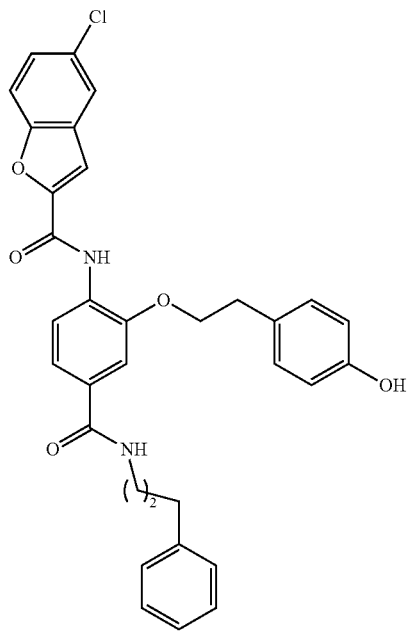
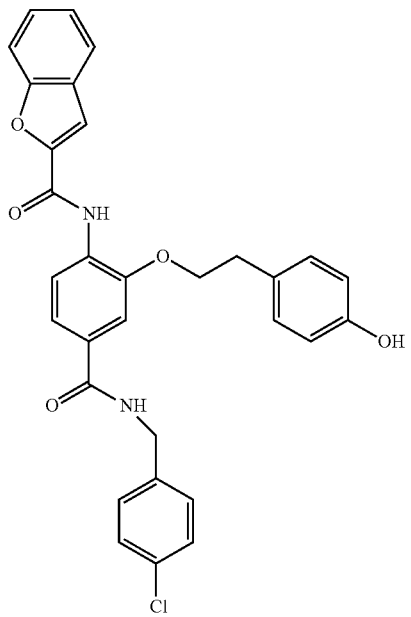

73
-continued
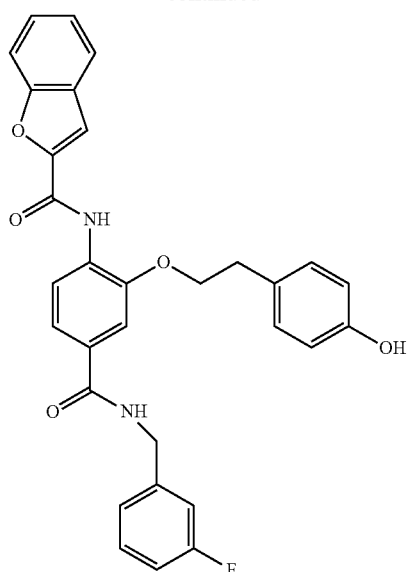
74
-continued
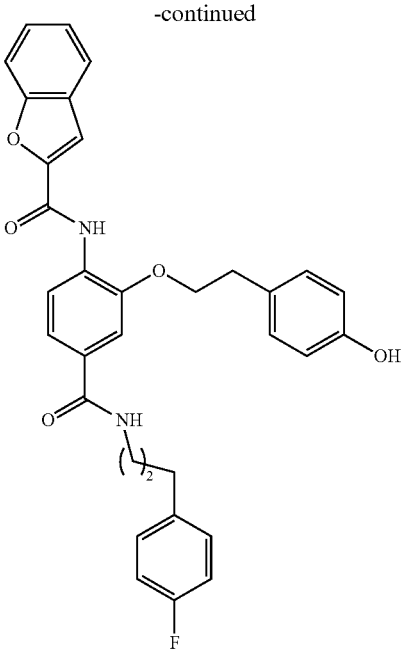
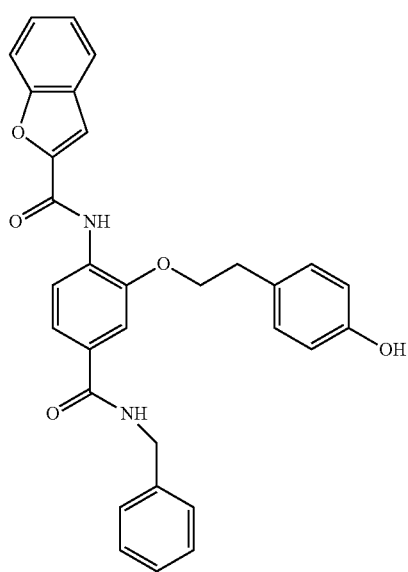
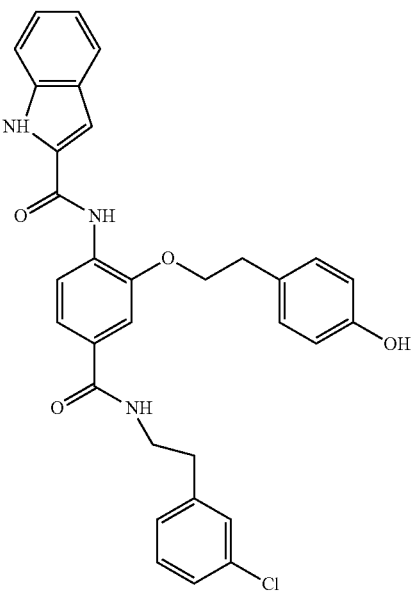

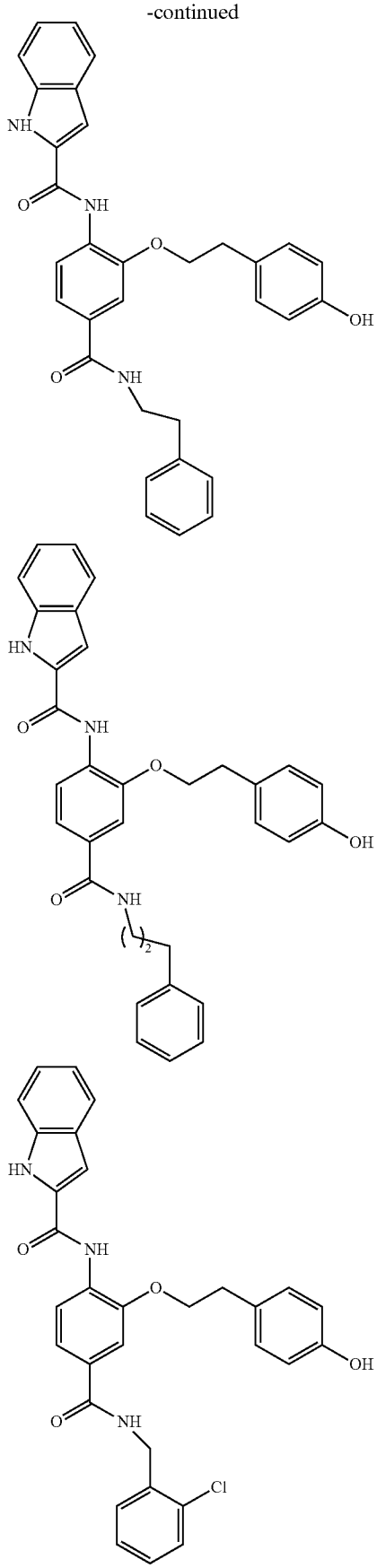
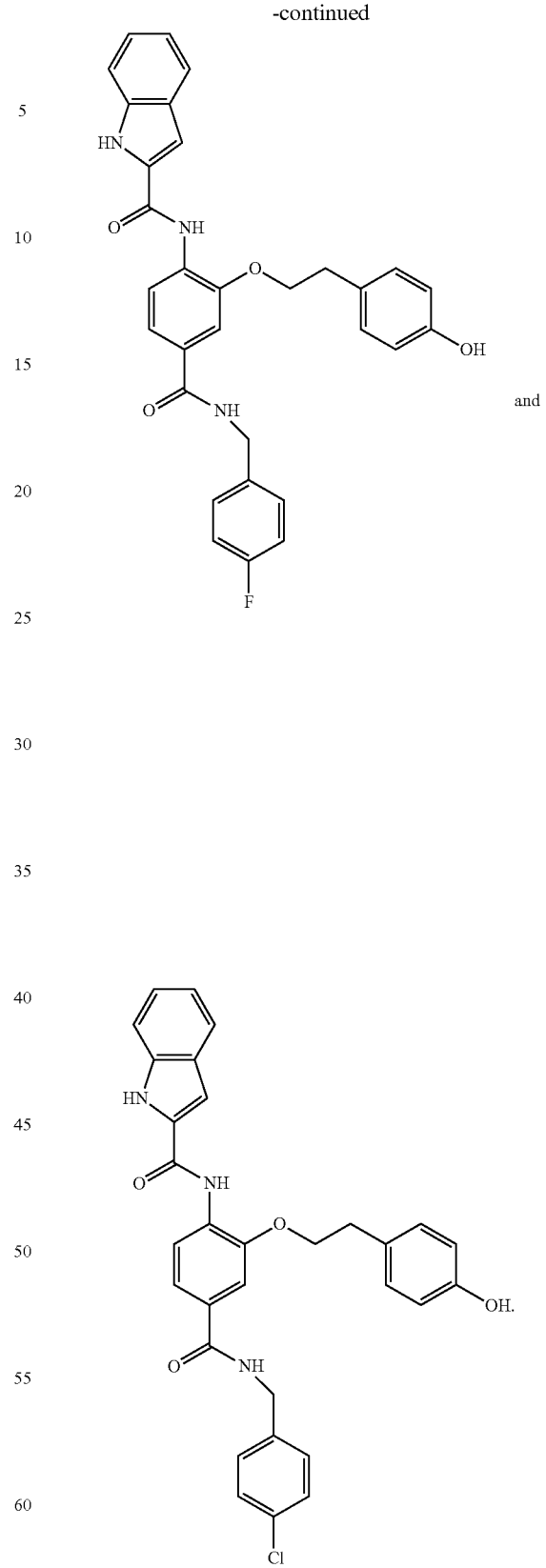
11. A compound corresponding in structure to the structural formula below, or a pharmaceutically acceptable salt thereof 77
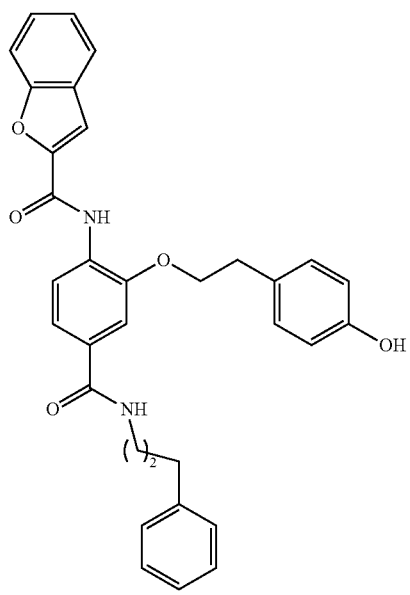
78
-continued
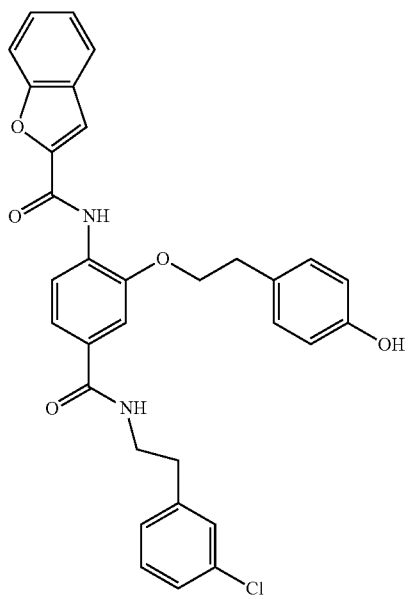
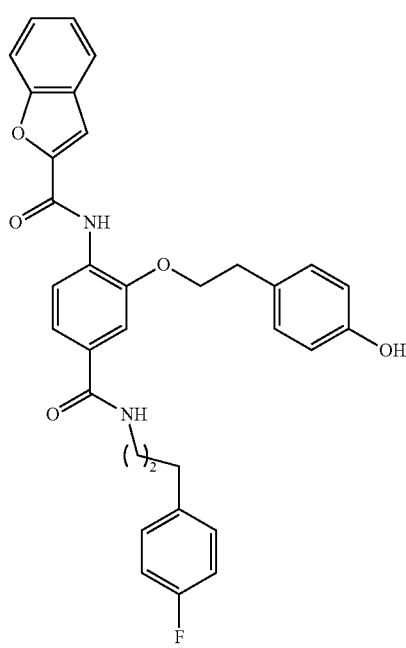
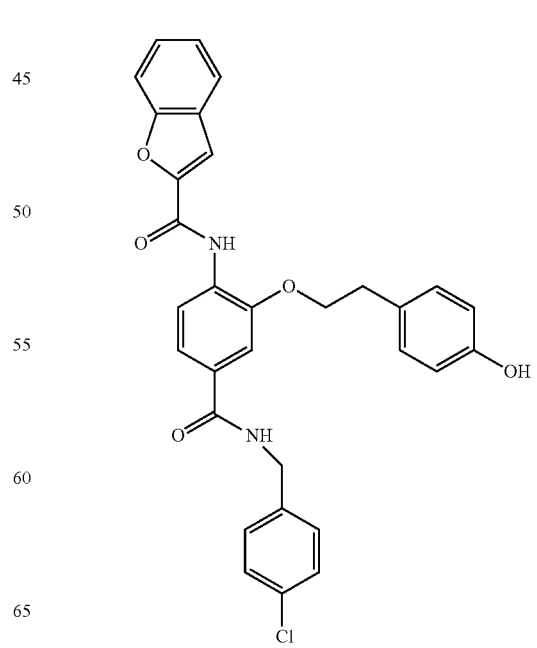

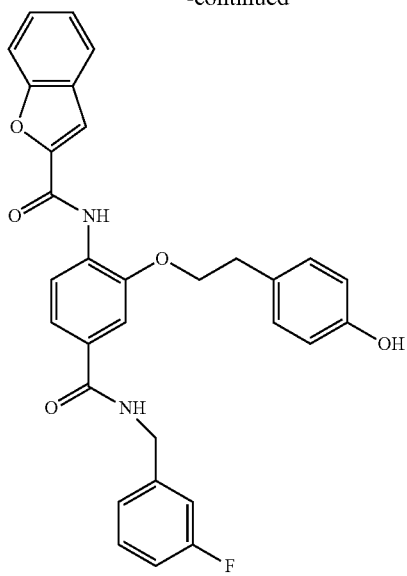

and

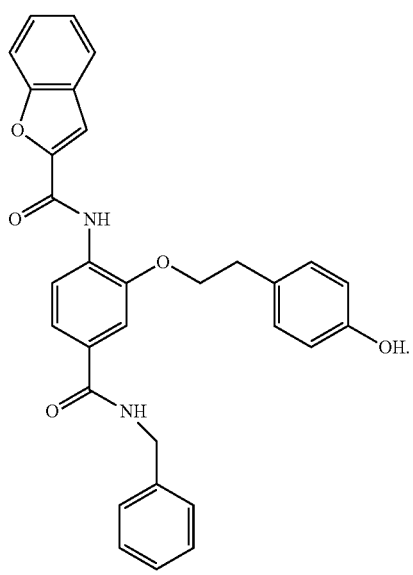

12. A pharmaceutical composition that comprises an adjuvant-effective amount of a compound of claim 1 or a pharmaceutically acceptable salt thereof dissolved or dispersed in a physiologically acceptable carrier.

13. An improved method of vaccination wherein mammalian cells in need of vaccination are contacted with an immunizing composition that comprises an effective amount of an immunogen and an effective amount of an adjuvant, wherein the improvement comprises use of a compound of claim 1 or a pharmaceutically acceptable compound salt thereof as the adjuvant.

14. The method according to claim 13, wherein said immunogen and said adjuvant are administered in the same composition.

15. The method according to claim 13, wherein said adjuvant corresponds in structure to a structural formula below, or a pharmaceutically acceptable salt thereof

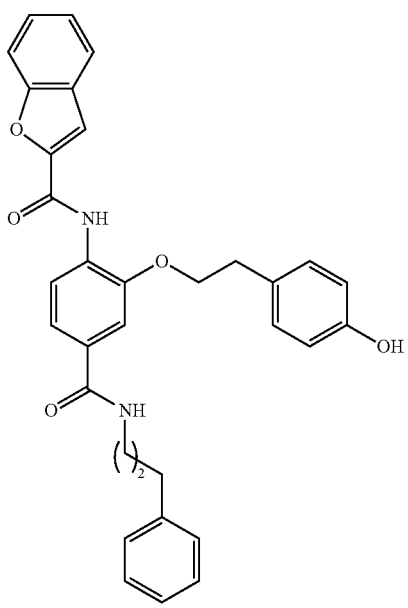

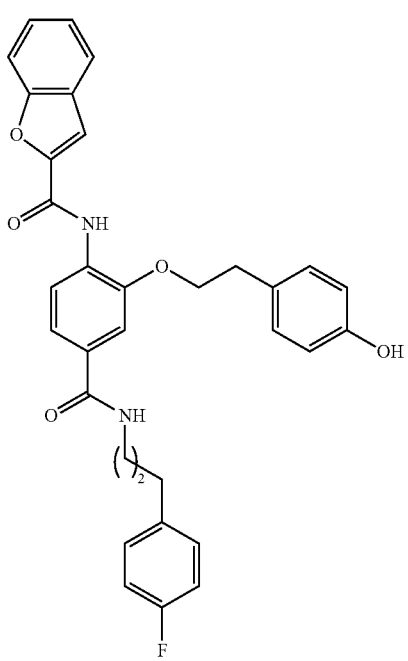

81
-continued
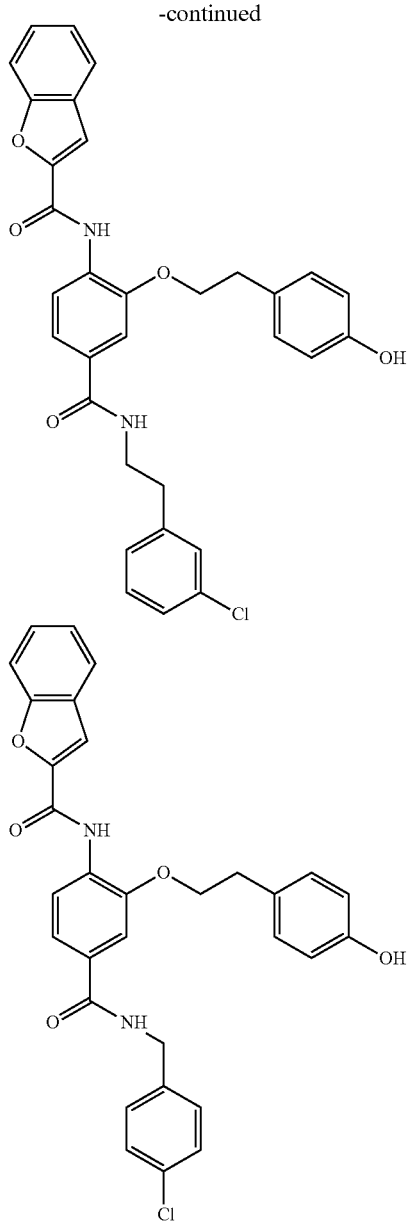
82
-continued
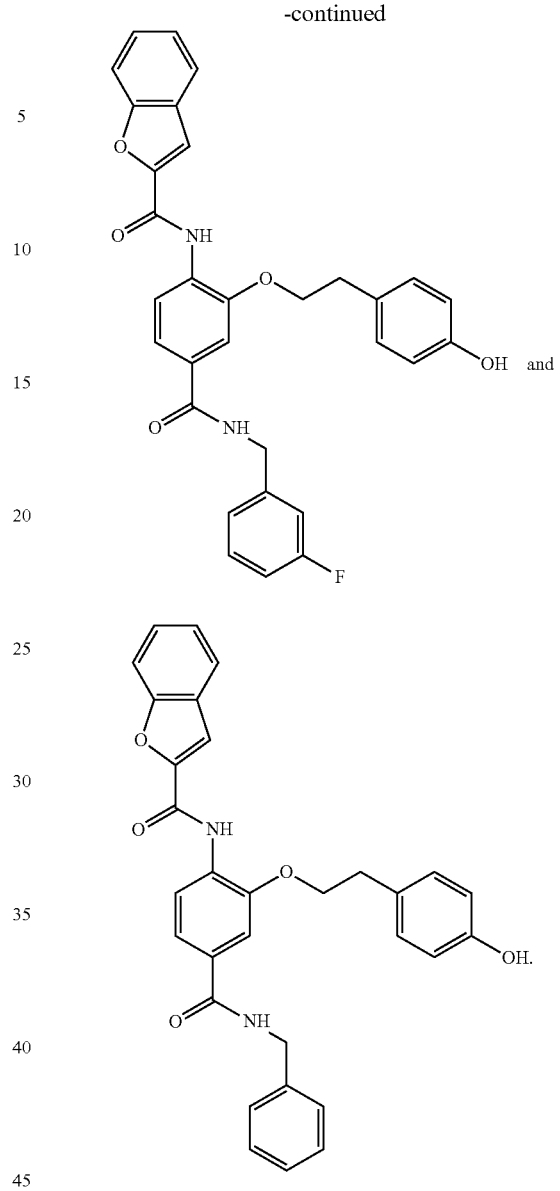
and
* * * * *

UNITED STATES PATENT AND TRADEMARK OFFICE
CERTIFICATE OF CORRECTION

PATENT NO. : 9,918,959 B2
APPLICATION NO. : 15/502117
DATED : March 20, 2018
INVENTOR(S) : Boger et al.

Page 1 of 1

It is certified that error appears in the above-identified patent and that said Letters Patent is hereby corrected as shown below:

In the Specification

Column 1, Lines 11-16, the paragraph GOVERNMENTAL SUPPORT should be changed to:
-- STATEMENT OF GOVERNMENT LICENSE RIGHTS
This invention was made with government support under grant number AI082657 awarded by the National Institutes of Health. The government has certain rights in the invention. --

Signed and Sealed this
Fifth Day of May, 2020

Andrei Iancu
*Director of the United States Patent and Trademark Office*